United States Patent
Galleguillos et al.

(10) Patent No.: US 6,410,005 B1
(45) Date of Patent: Jun. 25, 2002

(54) BRANCHED/BLOCK COPOLYMERS FOR TREATMENT OF KERATINOUS SUBSTRATES

(75) Inventors: Ramiro Galleguillos, Hudson; David J. Smith, Amherst; Steven A. Constantino, LaGrange; Daniel F. Hasman, Jr., North Royalton, all of OH (US)

(73) Assignee: PMD Holdings Corp., Cleveland, OH (US)

( * ) Notice: Subject to any disclaimer, the term of this patent is extended or adjusted under 35 U.S.C. 154(b) by 0 days.

(21) Appl. No.: 09/594,321

(22) Filed: Jun. 15, 2000

Related U.S. Application Data

(63) Continuation-in-part of application No. 09/223,664, filed as application No. PCT/US99/30790 on Dec. 22, 1999.

(51) Int. Cl.[7] .............. A61K 7/06; A61K 7/11; A61K 7/00; A61K 9/00; A61L 9/04
(52) U.S. Cl. ............... 424/70.16; 424/70.1; 424/70.11; 424/70.15; 424/70.122; 424/45; 424/47
(58) Field of Search ................ 424/70.1, 45, 47, 424/70.11, 70.16, 70.15, 70.122

(56) References Cited

U.S. PATENT DOCUMENTS

| | | |
|---|---|---|
| 3,907,984 A | 9/1975 | Calvert et al. |
| 3,914,403 A | 10/1975 | Valan |
| 3,925,542 A | 12/1975 | Viout et al. |
| 3,935,868 A | 2/1976 | Zeffren et al. |
| 3,937,811 A | 2/1976 | Papantoniou et al. |
| 3,954,960 A | 5/1976 | Valan |
| 4,007,005 A | 2/1977 | Patel |
| 4,030,512 A | 6/1977 | Papantoniou et al. |
| 4,085,167 A | 4/1978 | Lewis et al. |
| 4,130,517 A | 12/1978 | Lundberg et al. |
| 4,283,384 A | 8/1981 | Jacquet et al. |
| 4,604,440 A | 8/1986 | Wichterle et al. |
| 4,673,571 A | 6/1987 | Mahieu et al. |
| 4,764,363 A | 8/1988 | Bolich, Jr. |
| 4,902,499 A | 2/1990 | Bolich, Jr. et al. |
| 5,019,377 A | 5/1991 | Torgerson |
| 5,075,399 A | 12/1991 | Ahmed et al. |
| 5,104,642 A | 4/1992 | Wells et al. |
| 5,115,059 A | 5/1992 | Le |
| 5,196,495 A | 3/1993 | Chuang et al. |
| 5,206,009 A | 4/1993 | Watling et al. |
| 5,225,456 A | 7/1993 | Langerbeins et al. |
| 5,314,977 A | 5/1994 | Amick et al. |
| 5,360,867 A | 11/1994 | Sanchez |
| 5,373,044 A | 12/1994 | Adams et al. |
| 5,403,894 A | 4/1995 | Tsai et al. |
| 5,480,954 A | 1/1996 | Guo |
| 5,501,851 A * | 3/1996 | Mudge et al. |
| 5,565,193 A * | 10/1996 | Midha et al. |
| 5,599,524 A * | 2/1997 | Morawsky et al. |
| 5,618,524 A * | 4/1997 | Bolich, Jr. et al. |
| 5,620,683 A * | 4/1997 | Tong et al. |
| 5,622,694 A * | 4/1997 | Torgerson et al. |
| 5,632,998 A * | 5/1997 | Midha et al. |
| 5,653,968 A * | 8/1997 | Carballada et al. |
| 5,653,969 A * | 8/1997 | Carballada et al. |
| 5,658,557 A * | 8/1997 | Bolich, Jr. et al. |
| 5,662,892 A * | 9/1997 | Bolich, Jr. et al. |
| 5,665,337 A | 9/1997 | Carballada et al. |
| 5,667,771 A | 9/1997 | Carballada et al. |
| 5,686,062 A | 11/1997 | Tong |
| 5,686,067 A | 11/1997 | Shih et al. |
| 5,710,113 A | 1/1998 | Wells |
| 5,730,966 A | 3/1998 | Torgerson et al. |
| 5,733,537 A | 3/1998 | Halloran et al. |
| 5,753,216 A | 5/1998 | Leitch et al. |
| 5,807,545 A | 9/1998 | Coffindaffer et al. |
| 5,811,109 A | 9/1998 | Cooper et al. |
| 5,843,418 A | 12/1998 | Coffindaffer et al. |
| 5,855,878 A | 1/1999 | Coffindaffer et al. |
| 5,939,058 A | 8/1999 | Schwartz |
| 5,948,396 A | 9/1999 | Das et al. |
| 5,961,989 A | 10/1999 | Mougin et al. |

FOREIGN PATENT DOCUMENTS

| | | |
|---|---|---|
| DE | 1645232 | 10/1970 |
| DE | 3329765 C2 | 10/1993 |
| DE | 43 28 004 | 2/1995 |
| EP | 0 233 014 | 8/1987 |
| EP | 0 398 576 | 11/1990 |
| EP | 444 791 | 9/1991 |
| EP | 0 522 791 | 1/1993 |
| EP | 0 884 334 | 12/1998 |
| EP | 1068857 A1 * | 11/2001 |
| GB | 1 484 053 | 8/1977 |
| WO | WO9735544 * | 10/1997 |

OTHER PUBLICATIONS

Polymer Handbook, 3rd Edition, J. Brandrup et al., Interscience 1989.
"Contemporary Polymer Chemistry", 2nd Edition, H. Allcock et al., Ch. 17, Prentice Hall Publishers, 1990.

* cited by examiner

Primary Examiner—Thurman K. Page
Assistant Examiner—Hunera N. Sheikh
(74) Attorney, Agent, or Firm—Thoburn T. Dunlap; Hudak & Shunk Co., LPA

(57) ABSTRACT

A block copolymer for hair styling compositions includes hydrophilic and hydrophobic blocks which allow for optimization of desirable characteristics of the hair styling composition, such as flow onto the hair, prevention of curl droop, style retention at high humidity, tack, hardness, resistance to flaking, restylability, volumizing, and washability from the hair. The copolymer includes a polyacrylate backbone of hydrophobic blocks, with hydrophilic acrylate side chains. The copolymer is suitable for the formulation of a number personal care, household, hair care, skin care and other formulation. The copolymer is suited to incorporation into low VOC hydro-alcoholic hair styling compositions to meet reduced VOC, regulations.

55 Claims, 6 Drawing Sheets

Figure 3. Comparison of peak force versus time for virgin brown hair loops treated with A) Polyvinyl pyrrolidone, PVP; B) Polymer of Example 8 and C) copolymer of vinyl pyrrolidone with vinyl acetate, PVP/VA. Test conditions: 70% R.H.

Figure 4. Comparison of peak force versus time for restyled virgin brown hair loops treated with A) Polyvinyl pyrrolidone, PVP; B) Polymer of Example 8 and C) copolymer of vinyl pyrrolidone with vinyl acetate, PVP/VA. Test conditions: 8 mm compression at 70% R.H.

Figure 5. Comparison of peak force versus time for restyled virgin brown hair loops treated with A) Polyvinyl pyrrolidone, PVP; B) Polymer of Example 8 and C) copolymer of vinyl pyrrolidone with vinyl acetate, PVP/VA. Test conditions: 8 mm compression at 80% R.H. and 25°C.

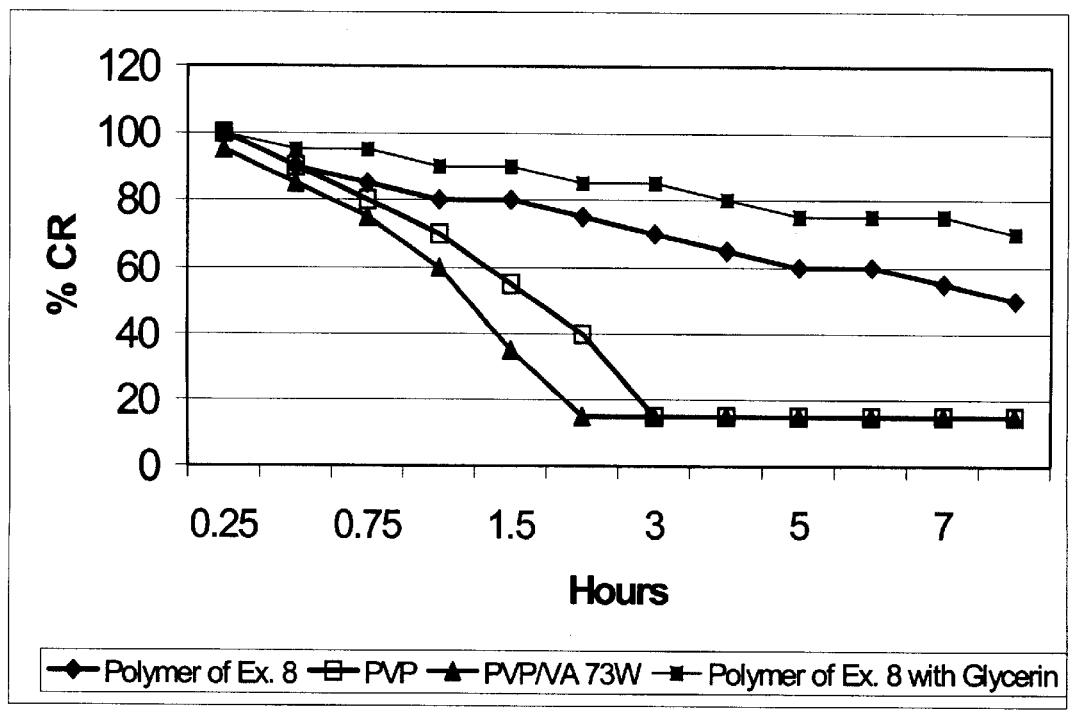
Figure 6. Comparison of the percentage Curl Retention of polymer of Example 8 versus PVP and PVP/VA. The top line is Polymer of Example 8 with glycerin. The level of ingredients in these compositions is listed on Table 10.

BRANCHED/BLOCK COPOLYMERS FOR TREATMENT OF KERATINOUS SUBSTRATES

CROSS REFERENCE

This application is a continuation-in-part of U.S. Ser. No. 09/223,664 filed Dec. 30, 1998, which claims benefits of PCT/US99/30790 Dec. 22, 1999.

BACKGROUND OF THE INVENTION

The present invention is directed to novel polymers containing a branched/block copolymer structure, which is useful for treatment of keratinous substrates, especially to cosmetic compositions, such as hair sprays, hair conditioners, hair setting lotions, creams, and the like, which incorporate the polymers. The polymers provide the cosmetic compositions with greater holding power, less flaking, and better ability to stylize than conventional polymers used in hair and similar cosmetic preparations.

Both natural and synthetic polymers, usually incorporated into an aqueous or an aqueous/alcoholic solution, are in current use as hair lacquers, hair-setting lotions, and the like. The function of such polymers is to impart "body" and holding power to the hair.

At the present time, the principal polymers or polymers employed in hair sprays, setting lotions, and hair conditioners include polyvinyl pyrrolidone (PVP) homopolymers and copolymers, half esters of polyvinyl ethers-maleic anhydride, polyvinyl acetate-crotonic acid co- and terpolymers, half esters of ethylene-maleic anhydride, acrylates and others.

With the exception of vinyl pyrrolidone homopolymers, conventionally employed synthetic polymers and polymers used in hair sprays, and the like, tend to impart excessive stiffness to the hair, causing an unnatural look. In addition, incorporation of such synthetic polymers or polymers into hair care compositions sometimes leads to excessive flaking, thereby making the compositions unsatisfactory from a commercial standpoint.

Although polyvinyl pyrrolidone homopolymers and copolymers provide a more natural look in that they are free from some of the disadvantages of other commercially available products, they tend to provide less satisfactory holding of the hair at high humidity levels. Typical hair styling polymers are random copolymers which are prepared by polymerizing two or more hydrophilic, anionic, cationic, or hydrophobic monomers, such as acrylic or vinyl monomers. The backbone of the resulting polymer is typically composed of a statistically random distribution of all the monomers. The ratio of these monomers is selected in such a way as to obtain a resin with a certain hydrophilic and hydrophobic balance.

The hydrophobic monomers generally provide better hairstyle retention at high humidity levels. Polymers, in which hydrophobic monomers predominate heavily, however, have poor solubility in water-ethanol mixtures, are not readily washable from the hair, and tend to flake and feel plastic-like on the hair. They are therefore unsuited to use in hair styling formulations.

On the other hand, polymers with high levels of hydrophilic groups have good solubility in water/ethanol mixtures and are washable from the hair. However, they are generally too sensitive to moisture, becoming tacky, and therefore do not hold a hairstyle under conditions of high humidity. U.S. Pat. No. 3,954,960 to Valan, for example, discloses a random copolymer of purely hydrophilic monomers. This is a film forming resin of a quatemized copolymer of vinyl pyrrolidone and a copolymerizable vinyl monomer such as a di-lower alkyl alkyaminoalkyl (or hydroxy alkyl)acrylate or methacrylate. Quaternized polymers of polyvinyl pyrrolidone, however, tend to be highly moisture sensitive and have overall poor performance in hairstyle retention and tack.

Accordingly, it is desirable to build a resin with a balance of hydrophilic and hydrophobic groups to achieve a combination of performance properties, such as style retention at high humidity, tack, hardness, flaking, washability from the hair, and other subjective performance attributes.

A typical example of a random copolymer having a hydrophilic/hydrophobic balance is disclosed in U.S. Pat. No. 3,914,403 to Valan. Valan discloses a film-forming resin formed from polyvinyl pyrrolidone, vinyl acetate, and a cationic monomer. The polyvinyl pyrrolidone and the cationic groups form the hydrophilic portion of the resin, while vinyl acetate provides the hydrophobic portion. By varying the ratio of polyvinyl pyrrolidone to vinyl acetate, water soluble or water insoluble polymers are obtained. The highly water soluble polymers tend to have poor hair style retention at high humidity, whereas the highly insoluble ones are likely to be un-washable and too plastic-like.

U.S. Pat. No. 3,925,542 to Viout, et al. and U.S. Pat. No. 5,196,495 to Chuang, et al. disclose additional examples of random copolymers with various hydrophilic/hydrophobic balances. Uses for the copolymers include aerosols, lacquers, non-aerosol hair sprays, hair setting creams, and setting lotions.

U.S. Pat. No. 4,007,005 to Patel discloses a hair setting resin based on a random copolymer of a reactive polyamide epichlorohydrin and polyvinyl pyrrolidone. The copolymer provides long style retention at high humidity. However, the reactive polymers are toxic and lack washability from the hair when used as aerosols, non-aerosol hair sprays and setting lotions.

Due to environmental regulations controlling the emission of volatile organic compounds (VOC's) into the atmosphere, VOC emissions have been restricted to 80% by weight of the hair styling formulation in some states, with further restrictions to 55% anticipated. To meet the regulations, reduced VOC hair styling formulations are being developed. Water is substituted for part or all of the organic solvents conventionally used in such formulations. U.S. Pat. No. 5,565,193 to Midha, et al. discloses a random copolymer hairstyling resin primarily formed from monomers such as n-butyl acrylate (the hydrophobic component), and acrylic acid, the (hydrophilic component), grafted with siloxane to balance the properties and to render the resin suitable for formulation in an 80% VOC composition. However, such polymers tend to become too soft and produce negative beading on the hair in low VOC formulations.

U.S. Pat. No. 5,620,683 to Tong, et al. discloses a resin comprising a random copolymer of n-alkyl acrylamide (the hydrophobic component) and acrylic acid (the hydrophilic component). Although the polymers are said to be suited to use in low VOC formulations, such polymers tend to be insoluble in water. Rather, they form a slurry in water and ethanol blends. Only upon adding the liquefied propellant gas, such as dimethyl ether, to the aerosol cans, does the resin dissolve. Preparing a slurry and pumping it into the aerosol cans is impractical for most purposes. In addition, because the resin is insoluble in water, it may prove difficult to wash from the hair.

U.S. Pat. No. 5,599,524 to Morawski, et al. discloses a hair spray composition in a formulation having 80% VOC's, or less. A defoaming agent is added to a conventional hair resin to reduce surface tension and to eliminate foaming of aerosol and non-aerosol hair sprays. The composition does not provide an improvement in flaking, fly away, or humidity resistance over conventional formulations.

U.S. Pat. No. 5,501,851 to Mudge, et al. discloses a random copolymer of butyl acrylate, methyl methacrylate, hydroxyethyl acrylate, and methacrylic acid for low VOC formulations. The polymer is dispersed in an emulsion to render it later removable with a shampoo.

The present invention provides for new and improved block/branched copolymers and hair treatment compositions incorporating the copolymers, which overcome the above-referenced problems, and others.

BRIEF DESCRIPTION OF THE DRAWINGS

FIG. 6 shows various degrees of curl retention when the hair is coated with various polymer formulations.

SUMMARY OF THE INVENTION

Figure 1:
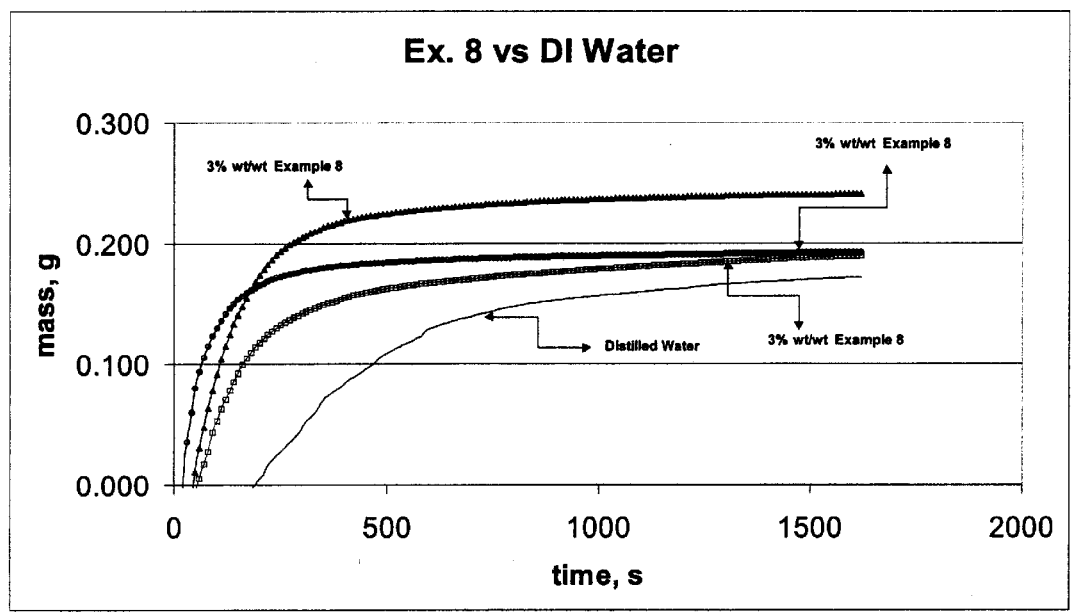
FIG. 1 shows the uptake by the hair of the polymeric solutions in comparison to the water.

The present invention has resulted from the discovery that a block copolymer for use in hair styling compositions can be prepared from ethylenically unsaturated monomers utilizing a polyfunctional organic monomer, having at least two functional groups, or chain extender monomer, where the reactivity of the functional groups is substantially different to produce an AB block copolymer. The polyfunctional monomer polymerizes with a first monomer or mixture of monomers through the functional group having the greater reactivity to form a first or A block. A second monomer or mixture of monomers contains at least one carboxylic acid group and copolymerizes with the less reactive functional group of the chain extender monomer to form a second, or B, block. The result is a block copolymer in which the A-block is more hydrophobic than the B-block so that the copolymer has both hydrophobic and hydrophilic blocks and has a plurality of glass transition temperatures and which provides exceptional utility as a hair styling composition.

In accordance with another aspect of the present invention, a hair styling composition includes about 1 to 20 weight percent of a block copolymer in accordance with the present invention, together with 20 to 99 weight percent of water and 0 to 80 weight percent of an organic solvent. In addition, a method of preparing a hair styling composition is provided. The method includes preparing an AB block copolymer having hydrophobic and hydrophilic blocks by polymerizing a polyfunctional organic monomer(s) which has at least two functional groups with a first ethylenically unsaturated monomer(s) to form an A-Block, and then polymerizing a second ethylenically unsaturated monomer (s) containing at least one carboxylic acid group with the A-block to form a B-block and a copolymer having hydrophobic and hydrophilic blocks. To prepare hair styling compositions 1–20% wt. of the block copolymer is combined with 20–97% wt. of water, 0 to 80% wt. of organic solvent, 0 to 5% wt. surfactant and conditioning agents, 0 to 1% wt. fragrance, and other ancillary agents.

One advantage of the present invention is that it enables hair styling compositions to be prepared with optimal performance properties, such as style retention at high humidity, prevention of curl droop, restylability without additional application, ability to increase hair volume, tack, hardness, flaking, washability from the hair and other subjective performance attributes.

Another advantage of the present invention is that the copolymers provided can be incorporated into hydro-alcoholic hair styling formulations to meet reduced VOC regulations and they are effective as styling agents in a wide variety of hair styling formulations, including aerosol sprays, mousses, spritzes, gels, setting lotions, and the like.

Yet another advantage of the present invention is that the copolymers can be used for a variety of other applications where a coating composition or film forming polymer would be employed which can benefit from the fact that the block copolymer has hydrophobic and hydrophilic blocks.

DETAILED DESCRIPTION OF THE PREFERRED EMBODIMENTS

A-Block/branched copolymer having two or more distinct glass transition temperatures ($T_g$) can be tailored to provide the desired properties in a hair care composition. The copolymer has a block structure, consisting essentially of a hard, hydrophilic block, which contributes to a high $T_g$, and a soft, more hydrophobic block, which contributes to a low $T_g$. The hydrophobic block forms the A-Block of the copolymer, while the hydrophilic block forms the B-Block. The hydrophilic B-Block and hydrophobic A-Block contribute different properties to the overall copolymer. The soft, low-$T_g$ hydrophobic A-Block contributes properties such as the formation of a uniform, clear film on the surface of the hair, providing high humidity resistance for durable hair style retention, conditioning and detangling the hair while wet, conferring the dried hair with a soft feel to the touch, adherence to the hair without flaking, reshaping of the hair by application of a curling iron. The hard, high-$T_g$, hydrophilic block provides the copolymer with benefits such as ease of dispersion of the copolymer in water, alcohol, or mixtures thereof, provision of a firm hold when applied to the hair, ease of washability from the hair, and detangling of the wet hair with a comb. These properties can be tailored by varying the composition and length of the blocks. For hair styling and fixing compositions, the hydrophobic A-Block is preferably a polyacrylate, while the hydrophilic branches are preferably formed from methacrylic acids or other polymer-forming carboxylic acids.

The general structure of the copolymer of this invention can be represented by the following two structures:

Structure 1

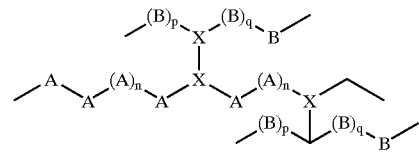

Structure 2

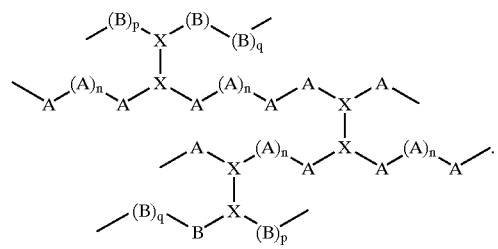

where A represents the monomer or monomers of the first block, referred to herein as the "A-Block," and B represents the monomer or monomers of the second block, referred to herein as the "B-Block." X represents a chain branching agent or a multifunctional monomer used to link the A and B-Blocks. In these structures, n represents the degree of polymerization of the A-Block, i.e., the number of monomer units in the A-Block. Its value is typically larger than 100. The letters q and p represent the degree of polymerization of the B-Block, i.e. the number of monomer units in the B-Block. Their added value is typically larger than 100. Either q or p can take the value of zero but not both at the same time. The straight line between two monomers (A—A) represents a covalent chemical bond.

The copolymers of this invention, as represented in Structures 1 and 2 above, are blocky and may form three-dimensional networks. The existence of the two blocks was confirmed by conducting differential scanning calorimetry on dry polymer samples. It is well known that the presence of two or more transition temperatures, $T_g$'s, is a clear indication of the blocky character of the copolymers, see, e.g., "Contemporary Polymer Chemistry" $2^{nd}$. Edition by H. Allcock and F. Lampe, Ch. 17, Prentice Hall Publishers, 1990. The A-Blocks and the B-Blocks are covalently or chemically attached through the chain branching agent X.

The average molecular weight of the copolymer can reach up to 1,000,000. The preferred molecular weight is in the 20,000 to 400,000 range and the most preferred from 50,000 to 250,000. The preferred molecular weight of the A-Block is in the range of 10,000 to 150,000, whereas the preferred molecular weight of the B-Block is in the range of 1,000 to 50,000.

Therefore, the copolymers of this invention attain their unique hair styling and fixing properties attributes due to a combination of soft and hard blocks. The A-Block is a soft more hydrophobic block, with low $T_g$, and the B-Block is a hard, hydrophilic high $T_g$ block. In addition, the length and composition of the blocks of the polymer can be varied to improve specific performance needs. In particular, the copolymers of this invention are designed to provide long lasting hair style retention at high humidity, natural feel, good hair combing, reduced flaking, no build up, and good hair styling and restyling. They are good film formers, water and alcohol soluble or dispersible and washable with water and shampoo.

To form the copolymer of the present invention, a two-step reaction process is used. This polymerization can be performed in a single reactor without having to isolate either the A or B-Block as an intermediate. The first step yields the A-Block portion of the copolymer, while the second step adds on the B-Blocks to form the resulting copolymer. In the first step, the monomers A, such as an acrylate, methacrylate, or a vinyl monomer, is copolymerized with a relatively small amount of the second chain extender monomer X. The monomer X has two or more polymerizable functional groups. The reactivity of the functional groups is such that the first monomer A reacts preferentially with a first functional group leaving the second functional group predominately unreacted. A preferred monomer X has both allyl and acrylate and methacrylate groups, for example, allyl methacrylate. The acrylate and methacrylate groups polymerize faster, due to its higher reactivity relative to the allyl groups. In the first step, the allyl groups remain predominantly unreacted.

The first and second monomers react to produce a polymer. The polymer may be a linear or a branched polyacrylate with allyl functional side arms.

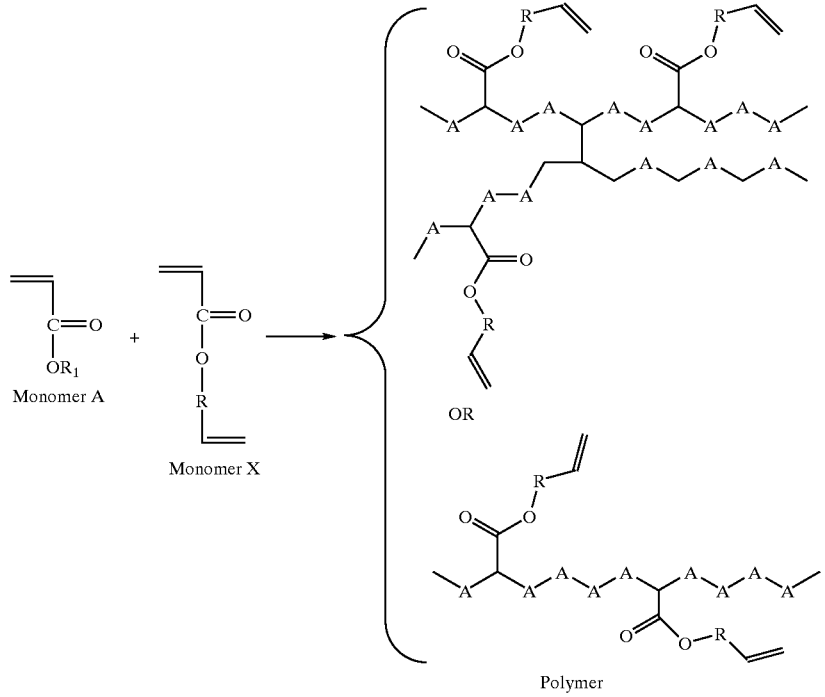

where R and $R_1$ are chemical groups described later and where A represents the incorporated monomer A. While two structures for the polymer have been shown, it should be understood that combinations of the two structures, including linear and branched portions, may be formed.

In the second step, monomers B, such as an acrylic or methacrylic acrylate or methacrylate monomer, is added and reacted with the slower reacting, second functional groups of the polymer to obtain a three-dimensional branched and blocky copolymer.

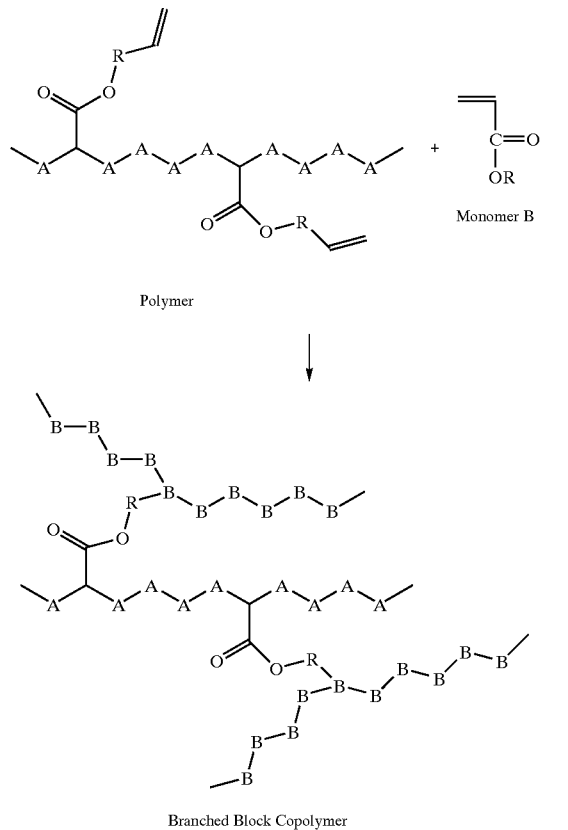

where R2 is preferably an alkyl group and B represents the incorporated monomer B. The copolymer thus has a backbone, primarily derived from the monomers A and branches derived primarily from the monomer B.

This method is not limited to preparing the hydrophobic monomer Block first with the multifunctional monomer, then preparing the hydrophilic B-Block. The order of addition can be changed. This is obvious to those familiar with the art of polymerization.

The B-Block of the copolymer is a hydrophilic block, while the A-Block is more hydrophobic than the B-Block. The hydrophobicity of the A-Block can be taylored to suit specific performance by incorporating hydrophilic monomers such as where the hydrophilic monomers is less than 60% mol.

Suitable hydrophobic monomers A include those which are a) water insoluble, that is, less than 0.2 weight percent of the hydrophobic monomer will dissolve in one hundred weight parts water at room temperature, and b) are ethylenically unsaturated compounds.

The hydrophobic monomers A preferably have at least 2 to 30 carbon atoms and are most preferably pendant organic groups such as:

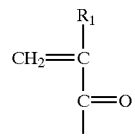

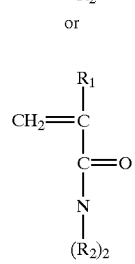

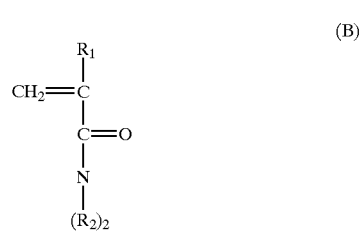

where $R_1$=—H, —$CH_3$, —$CH_2CH_3$, and $R_2$ is an aliphatic hydrocarbon group having at least two carbons, such as $C_2$ to $C_{20}$ alkyls and cycloalkyls; polynuclear aromatic hydrocarbon groups such as naphthyls, diphenyls, acenaphthenes, fluorenes, and the like; alkylaryls wherein the alkyl has one or more carbons, preferably 4 to 8 carbons; haloalkyls of 4 or more carbons, preferably perfluoroalkyls; polyalkyleneoxy groups wherein alkylene is propylene or higher alkylene and there is at least 1 alkyleneoxy unit per hydrophobic moiety. Exemplary hydrophobic monomers include the higher alkyl esters of α,β-ethylenically unsaturated carboxylic acids, such as methyl acrylate, methyl methacrylate, butyl acrylate, ethyl acrylate, octyl acrylate, dodecyl acrylate, dodecyl methacrylate, tridecyl acrylate, tridecyl methacrylate, tetradecyl acrylate, tetradecyl methacrylate, octadecyl acrylate, octadecyl methacrylate, ethyl half ester of maleic anhydride, diethyl maleate, and other alkyl esters derived from the reactions of alkanols having from 2 to 20, preferably from 2 to 8, carbon atoms with ethylenically unsaturated carboxylic acids such as acrylic acid, methacrylic acid, maleic anhydride, fumaric acid, itaconic acid and aconitic acid; alkylaryl esters of ethylenically unsaturated carboxylic acids such as nonyl -phenyl acrylate, nonyl-α-phenyl methacrylate, dodecyl-α-phenyl acrylate and dodecyl-α-phenyl methacrylate; N-alkyl, ethylenically unsaturated amides such as N-butyl acrylamide, T-butyl acrylamide, octyl acrylamide, N-octadecyl arylamide; N-octadecyl methacrylamide, N,N-dioctyl acrylamide and similar derivatives thereof; α-olefins such as octene-1, decene-1, dodecene-1 and hexadecene-1; vinyl alkylates wherein alkyl has at least 8 carbons such as vinyl laurate and vinyl stearate; vinyl alkyl ethers such as dodecyl vinyl ether and hexadecyl vinyl ether; N-vinyl amides such as N-vinyl lauramide and N-vinyl stearamide; and ar-alkylstyrenes such as t-butyl styrene.

Other suitable monomers A include N-substituted acrylamides or methacrylamides, substituted with alkyl radicals containing from 2 to 12 carbon atoms. Among the applicable acrylamides and methacrylamides are included N-ethyl acrylamide, N-tertiary-octyl acrylamide, N-decyl acrylamide, N-dodecyl acrylamide, as well as the corresponding methacrylamides.

Of the foregoing hydrophobic monomers, the alkyl esters of acrylic acid, methacrylic acid, N-alkyl acrylamides, and N-alkyl methacrylamides, wherein alkyl has from 2 to 8 carbon atoms, and the alkyl styrenes, wherein alkyl has from 4 to 8 carbons, such as t-butyl, are preferred. A particularly preferred monomer A is n-butyl acrylate, ethyl acrylate and 2-ethyl hexyl acrylate.

The chain branching monomers X used in formulating the copolymer:

a) should be multifunctional, i.e., should have at least two reactive, polymerizable, unsaturated functional groups, b) should contain a suitable combination of two or more unsaturated functional groups such as vinyl, allyl, acrylate, methacrylate in the same molecule.

Preferred chain branching monomers are those containing a combination of fast and slow reacting unsaturated groups. The fast reacting group is preferentially incorporated in the polymer backbone during the first step, whereas the slow reacting group reacts preferably in the second step.

The structure of the chain branching agent can be of the following type:

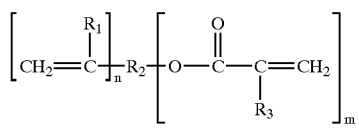

where n, m=1 to 4, m+n≧2

$R_1$, $R_3$=H, Alkyl of 1 to 22 carbons, preferably 1 to 3;

$R_2$=alkylene of 1 to 22 carbons, cycloalkylene of 3 to 6 carbons, arylene of 6 to 18 carbons, alkarylene of 7 to 24 carbons —$(CH_2—CH_2—O)_p$— where p=1 to 50, —$(CH_2(CH_3)—CH_2—O)_p$— where p=1 to 50, amido, ester, polyamido, polyester.

The reactivity of one of the functional groups should be relatively lower than the reactivity of the other. Table 1 below shows the reactivity ratios, r1 and r2, for allyl, acrylic and methacrylic functional groups; as defined in the Polymer Handbook, by H. Immergut and J. Brandrup, 3$^{rd}$ Edition, Interscience, 1989. It can be seen that the allyl groups react 3 to 10 times slower than the other groups.

TABLE 1

| Reactivities of Functional Groups | | |
|---|---|---|
| Fast Monomer/Slow Monomer | r1 | r2 |
| Acrylic Acid/Allyl Acetate | 0.500 | 0.061 |
| Methacrylic Acid/Allyl Acetate | 1.129 | 0.066 |
| Ethyl Acrylate/Allyl Acetate | 0.600 | 0.165 |
| Methyl Methacrylate/Allyl Acetate | 0.383 | 0.136 |
| n-Butyl acrylate/Allyl Acetate | 0.427 | 0.199 |

Other multifuinctional branching agents can also be used. Their selection should be based on the relative reactivity of their polymerizable groups. If the reactivity of the functional groups is substantially similar, then gelation during polymerization tends to occur. The polymer form is then difficult to remove from the reactor.

The monomers B are hydrophilic, or water-soluble monomers which are sufficiently water soluble to form at least a ten-weight percent solution when dissolved in water and readily undergo additional polymerization to form polymers which are water soluble. The monomers B preferably contain at least one available carboxylic acid group.

Exemplary hydrophilic monomers B include ethylenically unsaturated amides with chemical structure:

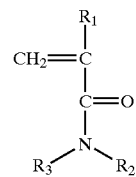

where $R_1$ is —H, —$CH_3$, —$CH_2$—$CH_3$, branched or linear alky, aryl, or cycloalkyl; $R_2$ and $R_3$ are —H, —$CH_3$, —$CH_2$—$CH_3$, branched or linear alkyl, aryl, or cycloalkyl; acid or salt functional, such as —$SO_3H$, —$SO_3M$ (where M=metal), or combinations thereof; amino functional such as:

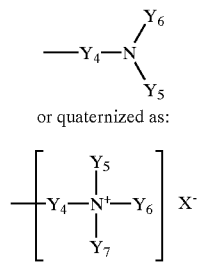

where $Y_4$, $Y_5$, $Y_6$, $Y_7$ are —H, —$CH_3$, —$CH_2$—$CH_3$, branched or linear alkyl, aryl, cycloalkyl, or combinations thereof.

$X^-$=an acid radical such as chloride, bromide, sulfate, sulfonate, phosphate, methyl or ethyl sulfonate, phosphate.

Examples include acrylamide, methacrylamide and fumaramide, and their N-substituted derivatives such as 2-acrylamido-2-methylpropane sulfonic acid (AMPS), N-(dimethylaminomethyl)acrylamide as well as N-(trimethylammonium-methyl)acrylamide chloride and N-(trimethylammoniumpropyl)-methacrylamide chloride.

Other ethylenically unsaturated water soluble heterocyclic amides with chemical structure:

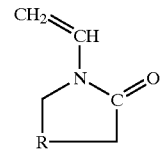

where R is an alkylene group such as —$[CH_2$—$]_n$, where n=1 to 4. Examples include vinyl pyrrolidone (n=1), vinyl caproclactam (n=2).

Other suitable water soluble monomers include ethylenically unsaturated carboxylic acids with general structure:

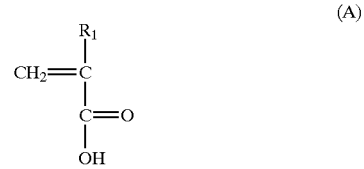

(A)

-continued $$\begin{array}{c} R_1 \\ | \\ CH_2=C \\ | \\ C=O \\ | \\ O \\ | \\ R_2 \\ | \\ C=O \\ | \\ OH \end{array} \quad (B)$$

$$\begin{array}{cc} CH=CH \\ | \quad | \\ O=C \quad C=O \\ | \quad | \\ OH \quad OH \end{array} \quad (C)$$

where $R_1$=—H, —$CH_3$, —$CH_2CH_3$ $R_2$=—$[CH_2$—$]_n$, where n=1 to 40's, linear or branched alkyl; cycloalkyl; aryl;

polyethylene oxide such as —($CH_2$—$CH_2$—O$)_p$— where p=1 to 50;

polypropylene oxide such as —($CH_2(CH_3)$—$CH_2$—O$)_p$— where p=1 to 50.

Examples include acrylic acid, methacrylic acid, maleic acid, itaconic acid and fumaric acid, vinylaryl sulfonates such as vinylbenzyl sulfonate as well as the salts of the foregoing monomers: ethylenically unsaturated quaternary ammmonium compounds such as vinylbenzyl trimethyl ammonium chloride, sulfoalkyl esters of unsaturated carboxylic acids such as 2-sulfoethyl methacrylate, and aminoalkyl esters of unsaturated carboxylic acids such as:

$$\begin{array}{c} R_1 \quad O \qquad Y_1 \\ | \quad \| \qquad / \\ CH_2=C-C-O-R_2-N \\ \qquad\qquad\qquad \backslash \\ \qquad\qquad\qquad Y_2 \end{array}$$

or their quaternized salts:

$$\begin{array}{c} R_1 \quad O \qquad Y_1 \\ | \quad \| \qquad | \\ CH_2=C-C-O-R_2-N^+-Y_2 \; X^- \\ \qquad\qquad\qquad | \\ \qquad\qquad\qquad Y_3 \end{array}$$

where $R_1$=—H, —$CH_3$, —$CH_2CH_3$;

$R_2$=—$[CH_2$—$]_n$, where n=1 to 40, linear or branched alkyl, cycloalkyl, aryl, polyethylene oxide such as —($CH_2$—$CH_2$—O$)_p$— where p=1 to 50, polypropylene oxide such as —($CH_2(CH_3)$—$CH_2$—O$)_p$— where p=1 to 50;

$Y_1$, $Y_3$, $Y_3$=—H, —$CH_3$, —$CH_2$—$CH_3$, branched or linear alkyl, aryl, cycloalkyl, or combinations thereof;

$X^-$=an acid radical such as chloride, bromide, sulfate, sulfonate, phosphate, methyl or ethyl sulfonate.

Examples include 2-aminoethyl methacrylate, N,N-dimethylaminoethyl methacrylate, N,N-dimethyl aminoethyl acrylate, 2-tert-butyl aminoethyl methacrylate, 2-trimethylammonium ethylmethacrylate chloride, 2-trimethylammonium ethylacrylate chloride, vinyl amines, such as vinyl pyridine and vinyl morpholine, diallyl amines and diallyl ammonium compounds, such as diallyl dimethyl ammonium chloride.

If monomers B are acidic, they make it possible for the resultant copolymer to be neutralized by reaction with an appropriate base so that the copolymer may exhibit a desirable level of water solubility. For example, the copolymer may be neutralized prior to being incorporated into an ultimate hair styling composition, allowing the composition to be removed from the hair simply by washing with water. Alternatively, if the copolymers are not pre-neutralized in this manner, removal may still be readily effected by application of an aqueous alkaline solution, such as soap in water.

The exact ratio of the monomers A and B is not critical to solubility. Copolymers with a high proportion of the hydrophobic A-Block can be dissolved in water by adjusting the pH.

In order to modify or enhance selected properties of the copolymer, for example, resistance to humidity, washability, and the like, the monomers A and B may be single monomers, or a combination of two or more monomers.

As for the actual preparation of the copolymer, any of the usual acrylate polymerization methods known in the art, such as solvent, suspension, emulsion, and inverse emulsion polymerization methods may be employed. In one preferred method of preparation of the copolymer, the monomers A, B. and X are reacted together in a suitable solvent. A free radical initiator is added in small quantities.

Suitable free radical initiators include azo- and peroxo-type initiators. Examples of azo-initiators are azobis-dimethylvaleronitrile, azobis-isobutyronitrile, azobis-methylbutyronitrile and others sold by DuPont, Wilmington, Del. under the trade name VAZO and by WAKO Pure Chemical Industries, Richmond, Va. under the trade name of V-40 to V501. Examples of peroxo initiators include di-T butyl peroxide, T-butyl cumyl peroxide, T-butyl peroxypivalate, lauryl peroxide, cumene hydroperoxide, ethyl hexyl peroxodicarbonate, diisopropyl peroxydicarbonate, 4-(t-butylperoxylperoxy-carbonyl)-3-hexyl-6-7-(t-butylperoxycarbonyl)heptyl cyclohexene (4-TBPCH), cumene hydroperoxide and t-butyl peroxyneodecanoate, t-butyl hydroperoxide, benzoyl peroxide and other organic peroxides sold by Elf Atochem North America, Inc., Philadelphia, Pa., under the trade names of Lupersol, Luperco, Lucidol and Luperox.

The initiator is preferably added at about 0.005 mole percent to 1 mole percent of the total monomer composition. Preferred initiators are di-T-butyl peroxide, T-butyl cymyl peroxide, T-butyl peroxypivalate, lauryl peroxide, cumene hydroperoxide, ethyl hexyl peroxodicarbonate, diisopropyl peroxydicarbonate, 4-(t-butylperoxylperoxy-carbonyl)-3-hexyl-6-7-(t-butylperoxycarbonyl)heptyl cyclohexene, cumene hydroperoxide and t-butyl peroxyneodecanoate, t-butyl hydroperoxide, benzoyl, peroxide and combinations thereof.

The polymerization can be carried in an variety of solvents, such alcohols, ethers, esters, aromatic solvents, glycols, glycol ethers, and glycol esters. Preferred solvents include ethyl alcohol, isopropyl alcohol, t-butyl alcohol, ethyl acetate, methyl acetate, butyl acetate, benzene, toluene, and methylene choride. These solvents can be used also in combination with hydrocarbon solvents such as hexane, cyclohexane, mineral spirits, and the like. One preferred solvent is an isopropyl alcohol and water mixture.

Preferably, a reaction vessel, containing the solvent is heated to a suitable polymerization temperature. The monomers A, B, and X are metered, as a mixture, into the reaction vessel, over a period of several hours. Optionally, the mixture of monomers is varied throughout the reaction period. The initiator, dissolved in an additional portion of the solvent, is simultaneously metered into the reaction vessel.

The resulting copolymer can be dried and ground into a powder, or used directly from solution.

The weight of each of the monomers in the mixture can vary, depending on the desired properties of the copolymer. In one preferred embodiment, the monomer A for A-Block comprises from about 28 to about 60% by weight of the mixture of monomers, the chain extender monomer X comprises from about 1 to about 1.5 by weight of the mixture, and the monomer B for B-Block comprises from about 38 to about 69% by weight of the mixture.

The copolymers are suitable additives for the formulation of hair fixative formulations, such as aerosol and non-aerosol hair spray, spritz, gel, spray gel, mousse, styling creams, hair relaxers, and the like. The copolymer is compatible with dyes and pigments suitable to prepare colored hair fixatives. Since the copolymers are soluble in water and alcohol mixtures, they are suitable for the formulation of reduced volatile organic compounds (VOC) fixative formulations. The copolymers can be used to prepare 80%, 55%, 30%, or less VOC, and alcohol free formulations.

The copolymer is also suitable for the preparation of shampoos, conditioners, rinses, liquid soap, soap bars, detergents, cleaners, room deodorizers, and the like.

The copolymers are also suitable additives for the formulation of hair and skin creams, lotions, pomades, and ointments; topical medicated creams, skin protective films, hair depilatories, hair shaving creams, hand and body lotions, mascaras, sunscreens, and such.

The copolymer also finds application as additive in nail care formulations such as water-based nail polish, nail repair, nail protection, and the like because it is a film forming polymer which is removable due to the polymer having both hydrophobic and hydrophilic group.

The copolymer can also be used advantageously in the formulation of pharmaceutical formulations such as creams, pomades, gels, tooth paste, tablets, gel capsules, enema fluids, vomitives, suppositories, foamed anti-fungal preparations, drug delivery compositions to deliver transdermally active ingredients to or through the skin, ocular fluids, anti-acne formulations, topical analgesics, and the like.

The block/branched copolymers can be used in a host of applications where the presence of polymeric blocks with different properties is a useful property. They can be used as additives in cosmetic applications, body implants, coatings for catheters, cannulae, antiperspirant and deodorant formulations, coating for medical devices, gloves, removable protective coatings, wound dressings, etc. They can be used in the formulation of inks, protective washable coatings for textiles, fabrics, metal strippers, and the like.

In particular, the polymers of this invention are designed to provide a combination of long lasting hair style retention at high humidity, natural feel, good hair combing, reduced flaking, no build up, and good hair stylability and restyling. They are good film formers, washable with water and shampoo.

Formulations incorporating the copolymers may be delivered from aqueous or hydro-alcoholic solutions, dispersions, or emulsions. The copolymers can be dissolved in water, water-ethanol or water-solvent mixtures by dispersing the copolymer in the solvent and adjusting the pH with an organic or inorganic base between pH3 and pH12. A preferred pH is 5.0 to 9.0. Within this pH range, water clear solutions of the copolymer can be prepared.

In preparing hair styling compositions which incorporate the copolymer, the copolymer, either in powdered or liquid form, is combined with a solvent system, or with a solvent/propellant system. Preferably, the copolymer comprises between about 0.01–20% by weight of the total weight of the composition, more preferably between 0.5–10% by weight. The solvent system preferably includes water and an organic solvent. Suitable organic solvents include alcohols, glycols and ketones, such as ethanol, isopropanol, acetone, dioxymethane, or methyl ethyl ketone, propylene glycol, hexylene glycol, and butylene glycol. For low VOC compositions, the solvent system preferably includes at least 20–50 weight percent water, and optionally up to 100% water. Preferably not more than about 25 weight percent of the organic solvent is used.

The hair styling compositions may be in the form of an aerosol or non-aerosol spray, a mousse, gel, or hair setting lotion. The compositions may contain up to 60 weight percent, preferably up to 35 weight percent, of liquified gases. Typical propellants include ethers, compressed gases, halogenated hydrocarbons and hydrocarbons. Exemplary propellants are dimethyl ether, compressed nitrogen, air or carbon dioxide, propane, butane, and 1,1 difluoroethane. Optionally, the solvent acts as the propellant.

The compositions may further include other materials or formulation additives, such as fragrances, preservatives, dyes and other colorants, plasticizers, emulsifiers, conditioners, neutralizers, glossifiers, lubricants, penetrants, UV absorbers, and the like. Mousses, according to the present invention, may fuirther comprise from about 0.25 to 6 weight percent, preferably 0.25 to 3 weight percent, of an emulsifier. The emulsifier may be nonionic, cationic, anionic, or amphoteric.

Formulation Additives

Examples of additives that are used in the formulation of hair, skin and nail products, include the following:
Conditioning Agents: In accordance with one important embodiment of the present invention, the composition of the present invention also includes from about 0.1% to about 10%, particularly about 0.5% to about 10%, and preferably from about 1.0% to about 5.0%, by weight of a non-volatile silicone compound or other conditioning agent(s), preferably a water-insoluble, emulsifiable conditioning agent. The preferred non-volatile silicone compound is a polydimethylsiloxane compound, such as a mixture, in about a 3:1 weight ratio, of a low molecular weight polydimethylsiloxane fluid and a higher molecular weight polydimethylsiloxane gum. The non-volatile polydimethylsiloxane compound is added to the composition of the present invention in an amount sufficient to provide improved combing and improved feel (softness) to the hair. As referred to herein, "silicone gums" are those nonfunctional siloxanes having a viscosity of from about 5 to about 600,000 centistokes at 25° C.
The so-called rigid silicones, as described in U.S. Pat. No. 4,902,499, herein incorporated by reference, having a viscosity above 600,000 centistokes at 20° C., e.g. 700,000 centistokes plus, and a weight average molecular weight of at least about 500,000 illustrated by the following formula:

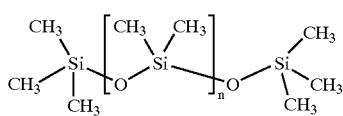

Such silicones are useful in accordance with the present invention. Preferred silicone gums include linear and branched polydimethylsiloxanes. Silicone gums useful in compositions of the present invention are available from a variety of commercial sources, including General Electric Company, Dow Coming and B.F.Goodrich.

Other conditioning agents are the 'so called' "dimethicone copolyols" and they may be linear or branched and may be block or random copolymers. Preferably, the dimethicone copolyols are block copolymers having one or more polysiloxane blocks and one or more polyether blocks, for instance ethylene oxide and propylene oxide.

Preferably, the weight ratio of ethylene oxide ($C_2H_4O$) to propylene oxide ($C_3H_8O$) in the dimethicone copolyols is from 100:0 to 35:65. The viscosity of the dimethicone copolyols as 100 percent actives at 25° C. is preferably from 100 to 4000 centistokes. The dimethicone copolyols are available from suppliers found in the International Cosmetic Ingredients Dictionary, 5th Edition, 1993, published by the CTFA in Washington D.C.

Another particularly suitable conditioning agent that can be included in the composition of the present invention is a volatile hydrocarbon, such as a hydrocarbon including from about 10 to about 30 carbon atoms, that has sufficient volatility to slowly volatilize from the hair after application of the aerosol or non-aerosol styling aid composition. The volatile hydrocarbons provide essentially the same benefits as the silicone conditioning agents. The preferred volatile hydrocarbon compound is an aliphatic hydrocarbon including from about 12 to about 24 carbon atoms, and having a boiling point in the range of from about 100° C. to about 300° C. Examples of volatile hydrocarbons useful in the composition of the present invention are the commercially-available compounds PERMETHYL 99A and PERMETHYL 101A, available from Permethyl Corporation, Frazer, Pa. A volatile hydrocarbon compound is useful in the composition of the present invention either alone, in combination with another volatile hydrocarbon, or in combination with a volatile silicone. Examples of other suitable water-insoluble conditioning agents that can be incorporated into the aerosol or non-aerosol aqueous styling aid composition of the present invention include the following: polysiloxane polyether copolymers; polysiloxane polydimethyl dimethylammonium acetate copolymers; acetylated lanolin alcohols; dimethyl dialkyl ammonium chlorides; modified alkyl dimethyl benzyl ammonium chlorides; lauryl dimethylamine oxide; stearyl dimethyl benzyl ammonium chloride; a lanolin-derived extract of sterol on sterol esters; lanolin alcohol concentrate; an isopropyl ester of lanolin fatty acids; sulfur rich amino acid concentrates; isopropyl ester of lanolin fatty acids; stearyl dimethyl benzyl ammonium chloride; cetyl trimethyl ammonium chloride; oleyl dimethyl benzyl ammonium chloride; oleyl alcohol; stearyl alcohol; stearyl dimethyl benzyl ammonium chloride; stearamidopropyl dimethyl myristyl acetate; a polyol fatty acid; a fatty amido amine; guar hydroxypropyltrimonium chloride; cetyl/stearyl alcohol; quaternized protein; keratin protein derivatives; isostearamidopropyl dimethylamine; stearamidopropyl dimethylamine; cetrimonium bromide; myrtrimonium bromide; stearalkonium chloride; cetyl trimethyl ammonium chloride; laurylpyridinium chloride; tris (oligoxyethyl)alkyl ammonium phosphate; an aminofunctional silicone; lapyrium chloride; isopropyl ester of lanolic acids; ethoxylated (30) castor oil; acetylated lanolin alcohol; fatty alcohol fraction of lanolin; a mineral oil and lanolin alcohol mixture; high molecular weight esters of lanolin; quatemium-75; vinylpyrrolidone/dimethylaminoethylmethacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of poly-hydroxycarboxylic acid; hydroxylated lanolin; cocamidopropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behenalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl dimethyl benzyl ammonium chloride; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryl-dimonium chloride; hydroxypropyl biscetyl-dimonium chloride; hydroxypropyl bisstearyl dimonium chloride; hydroxypropyl bisbehenyl dimonium chloride; ricinolamidopropyl ethyldimonium ethosulfate; olealkonium chloride; stearalkonium chloride; N-(3-isostearamidopropyl)-N,N-dimethyl amino glycolate; N-(3-isostearamidopropyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; sweet almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido morpholine lactate; wheat germamido dimethylamine lactate; behenamidopropyl betaine; ricinoleamidopropyl betaine; wheat germamidopropyl dimethylamine oxide; disodium isostearaimido MEA sulfosuccinate; disodium oleamide PEG-2 sulfosuccinate; disodium oleamide MEA sulfosuccinate; disodium ricinoleyl MEA sulfosuccinate; disodium wheat germamido MEA sulfosuccinate; disodium wheat germamido PEG-2 sulfosuccinate; stearalkonium chloride; stearly dimethyl benzyl ammonium chloride; stearamido amine; stearamido morpholine; isostearamido amine; isostearamido morpholine; polyethylene glycol (400) mono and distearates; synthetic calcium silicate; isostearic alkanolamide; ethyl esters of hydrolyzed animal protein; blend of cetyl and stearyl alcohols with ethoxylated cetyl or stearyl alcohols; amido amines; polyamido amines; palmityl amido betaine; propoxylated (1–20 moles) lanolin alcohols; isostearamide DEA; and hydrolyzed collagen protein. When one or more of these water-insoluble conditioning agents is included in the composition of the present invention in an amount of about 0.5% to about 10% by total weight of the composition, the composition also can include a suspending agent for the conditioning agent, in an amount of about 0.5% to about 10%, by total weight of the composition. The particular suspending agent is not critical and can be selected from any materials known to suspend water-insoluble liquids in water. Suitable suspending agents are for example, distearyl phthalamic acid; fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCutcheon's Detergents and Emulsifiers, 1989 Annual, published by McCutcheon Division, MC Publishing Co. A nonionic alkanolamide also is optionally included in an amount of about 0.1% to about 5% by weight in the styling aid compositions that include a conditioning agent to provide exceptionally stable emulsification of water-insoluble conditioning agents and to aid in thickening and foam stability. Other useful suspending and thickening agents can be used instead of the alkanolamides such as sodium alginate; guar gum; xanthan gum; gum arabic; cellulose derivatives, such as methylcellulose, hydroxybutylcellulose, hydroxyethylcellulose, hydroxypropylcellulose and carboxymethylcellulose; and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof.

Neutralizing Agents: In certain applications such as hair and skin care compositions, it is necessary to neutralize the hydrophilic B-block of the copolymer to achieve solubility or dispersibility and neutralization at times may increase crispness of the hair styling formulations. Neutralization and increased solubilization are accomplished, but not limited to, with one or more inorganic bases such as sodium hydroxide, potassium hydroxide, ammonium hydroxide and/or ammonium carbonate. Useful neutralizing organic bases are primary, secondary and tertiary amines and the water soluble alkanol amines such as monoethanolamine (MEA), diethanolamine (DEA), triethanolamine (TEA), 2-methyl-2-amino-1-propanol (AMP), 2-amino-2-methyl-propanol and 2-amino-2-methyl-1,3-propanediol, respectively, 2-dimethylaminoethanol N,N-dimethylethanolamine), 3-dimethylamino-1-propanol, 3-dimethylamino-2-propanol, 1-amino-2-propanol, and the like, monoamino glycols, and the like, which help solubilize the polymer in water solutions. The level of neutralization required for solubilization varies for each polymer. The block copolymers become soluble in water and hydroalcoholic solutions at 20% to 100% neutralization, and at all described levels of water/alcohol/ propellant solutions. The pH of these solutions usually ranges from 4 to 12 but generally will be between 5 and 8. The lowest neutralization level needed to render the polymer water soluble or dispersible depends on the composition of the block polymer, and the amount of alcohol, water, and propellant.

Aerosol Propellant Gas: The propellant gas included in the aerosol compositions of the present invention can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlorotrifluoroethane, dimethyl ether, propane, n-butane and isobutane, used singly or admixed. Water-soluble gases such as dimethyl ether, carbon dioxide, and/or nitrous oxide also can be used to obtain aerosols having reduced flammability. Water-immiscible, liquified, hydrocarbon and halogenated hydrocarbon gases such as propane, butane and chlorofluorocarbons can be used advantageously to deliver the contents of the aerosol container without the dramatic pressure drops associated with other immiscible gases. Here there is no concern for the head space to be left inside the aerosol container, because the liquified gas will sit on top of the aqueous formulation and the pressure inside the container is always the vapor pressure of saturated hydrocarbon vapor. Other insoluble, compressed gases such as nitrogen, helium and fully-flourinated oxetanes and oxepanes also are useful to deliver the compositions from aerosol containers. Other means of delivery of the above-described aqueous styling aid compositions include, pump sprayers, all forms of bag-in-can devices, in situ carbon dioxide ($CO_2$) generator systems, compressors, and the like. The amount of the propellant gas is governed by normal factors well known in the aerosol art. For mousses, the level of propellant is generally from about 3% to about 30%, preferably from about 5% to about 15% of the total composition. If a propellant such as dimethyl ether utilizes a vapor pressure suppressant (e.g., trichlorethane or dichloromethane), for weight percentage calculations, the amount of suppressant is included as part of the propellant.

Optional Additives: The hair styling compositions also can contain a variety of other nonessential, optional components suitable for rendering such compositions more aesthetically acceptable. Such conventional optional ingredients are well known to those skilled in the art, e.g., other emulsifiers such as anionics (e.g., sodium alkyl sulfate); preservatives such as benzyl alcohol, methyl paraben, propyl paraben iodopropenylbutyl carbamate, sodium benzoate, glutaric aldehyde and imidazolidinylurea; cationic emulsifiers/conditioners such as cetyl trimethyl ammonium chloride, stearyldimethyl benzyl ammonium chloride, and di(partially-hydrogenated tallow) dimethylammonium chloride; viscosity modifiers such as a diethanolamide of a long chain fatty acid, fatty alcohols (i.e., cetearyl alcohol), sodium chloride, sodium sulfate, and ethyl alcohol; pH adjusting agents such as citric acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as thioglycolates; perfume oils; chelating agents such as ethylenediaminetetraacetic acid; and, among many other agents, polymer plasticizing agents such as glycerin and propylene glycol. These optional materials are generally used individually at a level of from about 0.01% to about 19%, preferably from about 0.5% to about 5% by weight of the total composition. The aqueous formulations of the present invention also can contain the conventional hair spray adjuvants in amounts which generally range from about 0.1 to 2% by weight and preferably about 0.75 to 1% by weight. Among the additives which can be used are plasticizers such as glycols, phthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

The compositions of this invention may optionally contain one or more other fixative resins. Examples of other hair fixative resins include synthetic polymers such as polyacrylates, polyvinyls, polyesters, polyurethanes, polyamides and mixtures thereof;p polymers derived from natural sources such as modified cellulose, starch, guar, xantham, carragenan and blends thereof. These resins may have cationic, anionic, nonionic, ampholytic or switterionic in character. They may be soluble, dispersible or insoluble in water and hydroalcoholic formulations. Their glass transition temperature, Tg, may be in the range from −50° C. to 200° C.

Another class of organosilicones that may be advantageously incorporated in the hair styling compositions of this invention are silicone resins which are non-polar silsesquioxanes. These resins are film forming and aid in imparting good cure retention property to the composition. The silsesquioxanes have a formula selected from the group consisting of

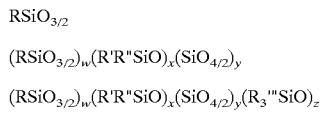

and hydroxy, alkoxy, aryloxy, and alkenoxy, derivatives thereof, wherein R, R', and R''', are selected from the group consisting of alkyl, alkenyl, aryl, and alkylaryl, radicals having from one to twenty carbon atoms; and w, x, y, and z, are each integers having a value of from zero to about one thousand, with the proviso that the sum of integers w and y must be at least one.

The nonpolar silsesquioxane silicone resin materials conforming to any one of the above specified generic formulas are commercially available from the Dow Coming Corporation, Midland, Mich.

These nonpolar silsesquioxanes can be incorporated into hair styling formulations containing the block copolymers of the invention provided a solvent, such as ethanol or any other appropriate solvent is present in the formulation, either above or in a mixture with water.

The organosilicone compound is present in the mixture at a level from about 0.1 to about fifty percent by weight based on the weight of the mixture. Preferably, the organosili-cone compound is present in the mixture at a level from about three to about thirty percent by weight based on the weight of the mixture. The solvent may be water, a hydrocarbon, an alcohol, or a blend of alcohol and water. Other solvents which may be employed include supercritical fluids such as supercritical carbon dioxide and nitrogen; volatile silicones including linear and cyclic siloxanes; non-volatile hydrocarbons; and in some instances, aqueous emulsion systems may also be appropriate. Where the solvent is hydrocarbon, it is preferred to employ materials such as dimethylether, liquefied petroleum gas, propane, and isobutane. In the event the solvent is an alcohol, some appropriate materials are methanol, ethanol, and isopropanol.

One example of a silsesquioxane may be represented by the formula

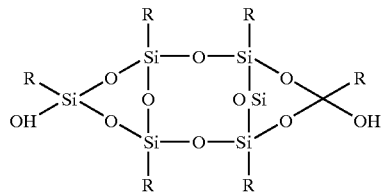

Another additive that may be incorporated into the instant hair compositions is a soluble surface tension reducing compound. It is any soluble compound which reduces the surface tension between the hair styling composition and the gaseous atmosphere above the hair styling composition. By "gaseous atmosphere" we mean a propellant or air. The soluble surface tension reducing compound may be for example a plasticizer or surfactant in the hair styling composition. The soluble surface tension reducing compound includes for example dimethiconecopolyols, panthenol, fluorosurfactants, glycerin POE, PPG 28 Buteth 35, PEG 75 lanolin, oxtoxynol-9, PEG-25 hydrogenated castor oil, polyethylene glycol 25 glyceryl trioleate, oleth-3 phosphate, PPG-5-ceteth-10 phosphate, PEG-20 methyl glucose ether, or glycereth-7-triacetate, glycereth-7-benzoate or combinations thereof. Preferably the soluble surface tension compound is dimethiconecopolyols, panthenol, glycereth-7-benzoate, or combinations thereof.

The soluble surface tension reducing compound is typically present in the low beading, low VOC hair styling composition at a concentration of from 0.01 to 1 weight percent, and more preferably at a concentration of from 0.01 to 0.25 weight percent, based on the total weight of the composition.

Also useful additives are plasticizing compounds. The first class of plasticizing compounds are soluble polycarboxylic acid esters. The polycarboxylic acid esters have a carbon backbone of from 3 to 12 carbon atoms and 3 or more $C_1$ to $C_5$ alkyl carboxylate groups attached thereto. Suitable polycarboxylic acid esters include, for example, triethyl citrate, tributyl citrate, triethyl phthalate, tributyl phthalate, tripentyl phthalate or combinations thereof. Preferably, the polycarboxylic add esters are selected from triethyl citrate, tributyl citrate, tributyl phthalate, or combinations thereof and more preferably are selected from triethyl citrate, tributyl citrate, or combinations thereof. The plasticizing compounds are preferably added to the hair styling composition to provide a total concentration of from 0.01 to 1.0 weight percent plasticizing compounds, more preferably 0.1 to 0.5 weight percent plasticizing compounds, based on the total weight of the hair styling composition.

The formulation may optionally contain one or more nonactive adjuvants in an amount up to about 5 wt. % based on the total composition. Such nonactive additives include a corrosion inhibitor, a surfactant, a film hardening agent, a hair curling agent, a coloring agent, a lustrant, a sequestering agent, a preservative and the like. Typical corrosion inhibitors include methylethyl amine borate, methylisopropyl amine borate, inorganic hydroxides such as ammonium, sodium and potassium hydroxides, nitromethane, dimethyl oxazolidine, 2-dimethylamino-2-methyl-1-propanol, and aminomethyl propanol.

Carrier Vehicle: Polar solvents are typically used to prepared the cosmetic or hair compositions. Water, glycols and alcohols are preferably used. The optional alcohol employed in the composition is an aliphatic straight or branched chain monohydric alcohol having 2 to 4 carbon atoms. Isopropanol and especially ethanol are preferred. The concentration of the alcohol in the composition should be less than about 40% by weight, and surprisingly can be as low as 0%, preferably 0–30% by weight and more preferably 5–20% by weight. Some alcohol, in an amount of about 2% to about 10% by weight.

In preparing the hair styling compositions of the present invention, the copolymer is optionally neutralized to the extent that from about 40 to 100 mole percent of the carboxylic groups in the copolymer are neutralized by a neutralization agent, in a solvent system wherein water is the primary solvent. At neutralizations greater than around 92%, the humidity resistance of the hair styling composition is greatly reduced.

The hair styling compositions incorporating the branched block copolymer exhibit desirable characteristics of such compositions, including long lasting hair style retention at high humidity, natural feel, good hair combing, reduced tack, reduced flaking, good stylability and restyling, no fly away, and the like.

A non-aerosol, low VOC, pump hair spray composition is provided herein which is capable of being applied by the user as a fine spray mist, which dries rapidly on the hair, and which provides low curl droop and effective curl retention properties thereon. The composition consists essentially of a block copolymer of this invention as a hair fixative polymer, and a mixture of alcohol, water and dimethoxymethane (DMM) as cosolvents therefor. Such formulations may be prepared as anhydrous formulas as well as all water systems, and both as hair sprays or as mousse products. For these applications, it is preferable to use lower molecular weight block copolymers and the sprayed droplets size should be as small as practical to achieve fast drying of the film. The block copolymers of this invention perform substantially better as the conventional fixative polymers because these block copolymers inhibit the curl droop to a greater extent than other polymers used in such formulations. Preferably, the hair fixative polymer is present at a solids level of about 1–15%, the alcohol in an amount of about 50–70%, water at 10–30%, and DMM at 10–30%, by weight of the composition.

Other applications for the polymers of the present invention would include: adhesive, metal cleaners, oil/gas well cleaners, preservative intermediate, polystyrene manufacture, surface cleaners, industrial cleaners, coatings, industrial, coatings, specialty and imaging, paint stripper, printing inks, photo-resist applications, paints/latex systems, battery manufacture, reaction solvent and fiber dying, detergents, textile dye stripping, printed circuit boards, dispersants, gel former, petrochemical processing, and paper manufacture.

While not intended to limit the invention, the following examples are illustrative of the methods of preparing the copolymers and hair styling compositions, and of their unique styling properties.

General Method Of Preparation Of Polymers

The following method was used to prepare a variety of copolymers. A clean, dry 8 liter glass reactor was set up in a heated waterbath and fitted with a condenser and a stirring agitator. To the reactor, 1750 grams of solvent, a mixture of 80% isopropyl alcohol and 20% water, was charged and heated to reflux temperature (78–82° C.). A first batch, or feed of monomers for forming the A-Block, 1200 grams of n-butyl acrylate, and 116 grams of methacrylic acid, and 20 grams of a chain extender, allyl methacrylate, were mixed together and charged into a storage cylinder connected to the reactor by a feed line and a metering pump. 16.8 grams of an initiator, t-butyl peroxypivalate were diluted with a further 200 grams of solvent and charged to another storage cylinder also connected to the reactor by a metering pump.

After the reactor reached reflux temperature the polymerization was started. The first batch of monomers was fed in evenly over a one hour period and the initiator was fed in over evenly over a four hour period. After the first hour, a second batch, or feed, of monomers for forming the B-Block, a blend of 1053 grams of methacrylic acid and 10 grams of allyl methacrylate chain extender was fed into the reactor evenly over a two hour period. The total monomer feed time was three hours and the total initiator feed time was four hours. After all the ingredients had been added, the reactor was held at reflux temperature for another two hours before cooling to room temperature. The resulting reaction mixture comprised 50 percent solids by weight.

The above method was used to prepare copolymers of varying compositions. The molecular weight (Mw) of the polymers was measured by gel permeation chromatography, GPC. The $T_g$ of the polymers was measured using differential scanning calorimetry, DSC. Table 2 summarizes the quantities of the three monomers used in preparing each of the copolymers, in terms of the weight added in each of the two feed mixtures, and the total weight of monomer added in both the mixtures. The percentage solids in the reactor at the end of the reaction period is included for each of the copolymers prepared, together with the high and low glass transition temperatures of the copolymer, and the molecular weight of the copolymer.

Key for the Examples of Polymers

In the examples, the following abbreviations will be used:

| | | |
|---|---|---|
| nBA | = | n-butyl acrylate |
| All MA | = | (chain extender) allyl methacrylate |
| AA | = | acrylic acid |
| MAA | = | methacrylic acid |
| EGDMA | = | (chain extender) ethylene glycol dimethacrylate |
| Lup-11 | = | (initiator) t-butyl peroxypivalate (Lup-11 is short for Lupersol-11, and is available from Atochem North America, Inc.) |
| IPA/H$_2$O | = | (solvent) at 80/20 wt % mixture of isopropyl alcohol/water |
| Tg 1 | = | Low glass transition temperature |
| Tg 2 | = | High glass transition temperature |
| phm | = | parts per hundred parts of monomer |
| Mw | = | weight average molecular weight |

Substantiation Examples of Block/Branched Copolymers with Two Tg

The copolymers in Examples 1 to 3 were prepared following the polymerization scheme above. The A-block was prepared using two monomers and the B-block contains only one. The A-Block is predominantly hydrophobic; the B-block is hydrophilic and ionizable. The molecular weight Mw of the polymers was measured by gel permeation chromatography, GPC. The Tg of the polymers was measured using differential scanning calorimetry, DSC.

TABLE 2

| | | Monomer Composition | | | | |
|---|---|---|---|---|---|---|
| | | A-Block | B-Block | Total Batch | | Observa- |
| Example | Ingredient | (g) | (g) | (g) | phm | tions |
| 1 | AA | 216.00 | 1944.00 | 2160.00 | 60.00 | |
| | n-BA | 1386.00 | 0.00 | 1386.00 | 38.50 | Mw = 88,900 |
| | All MA | 36.00 | 18.00 | 54.00 | 1.50 | Tg 1 = −13.7° C. |
| | Lup - 11 | 18.00 | | 18.00 | 0.50 | Tg 2 = 97° C. |
| | IPA/H2O | | | 2400.00 | 66.66 | |
| 2 | AA | 162.40 | 1461.60 | 1624.00 | 70.00 | |
| | n-BA | 661.20 | 0.00 | 661.20 | 28.50 | Mw = 67,500 |
| | All MA | 34.80 | 18.00 | 52.80 | 1.50 | Tg 1 = 19° C. |
| | Lup - 11 | 16.24 | | 16.24 | 0.50 | Tg 2 = 106° C. |
| | IPA/H2O | | | 2400.00 | 66.66 | |
| 3 | MAA | 175.00 | 1580.00 | 1755.00 | 48.75 | |
| | n-BA | 1800.00 | | 1800.00 | 50.00 | Mw = 59,200 |
| | All MA | 30.00 | 15.00 | 45.00 | 1.25 | Tg 1 = −17° C. |
| | Lup - 11 | | | 25.2 | 0.70 | Tg 2 = 145° C. |
| | IPA/H2O | | | 2400.00 | 66.66 | |

Examples to Substantiate the Criticality of Using a Suitable Chain Extender

To demonstrate the blocky-structure of the polymer and the importance of using a suitable chain extender, block copolymers were prepared where the A-block was a hydrophobic, water-insoluble block and the B-block, hydrophilic and ionizable. Examples 4 and 5 were prepared in a similar manner, without and with allyl methacrylate, All MA (the chain extender monomer), respectively. The hydrophobic block of Polymer 4, after neutralizing with base at high pH, did not dissolve in water. The polymer formed a milky, phase-separated suspension. Conversely, the polymer of Example 5, which includes All MA, formed a water clear solution after neutralization with base at pH=7.16.

TABLE 3

|  |  | Monomer Composition | | | |
|---|---|---|---|---|---|
|  |  | A-Block | B-Block | Total Batch | |
| Example | Ingredient | (g) | (g) | (g) | phm |
| 4 | MAA | 446.00 | 1354 | 1800.00 | 60.00 |
|  | n-BA | 1200.00 | 0.00 | 1200.00 | 40.00 |
|  | All MA | 0 | 0 | 0 | 0 |
|  | Lup - 11 |  |  | 21.00 | 0.70 |
|  | IPA/H2O |  |  | 3000.00 | 100.00 |
| 5 | MAA | 446.00 | 1316.5 | 1762.5 | 58.75 |
|  | n-BA | 1200.00 | 0.00 | 1200.00 | 40.00 |
|  | All MA | 25.0 | 12.5 | 37.5 | 1.25 |
|  | Lup - 11 |  |  | 21.00 | 0.70 |
|  | IPA/H2O |  |  | 3000.00 | 100.00 |
| 6 | MAA | 446.00 | 1316.5 | 1762.50 | 58.75 |
|  | n-BA | 1200.00 | 0.00 | 1200.00 | 40.00 |
|  | EGDMA | 25.00 | 5.0 | 30.00 | 1.00 |
|  | Lup - 11 |  |  | 30.00 | 1.00 |
|  | IPA/H2O |  |  | 3000.00 | 100.00 |

Resin of Example 6 was prepared using ethylene glycol dimethacrylate, EGDMA, a difunctional chain extender whose reactive groups have comparable reactivity. The resulting polymer was heavily cross-linked and formed a solid gelled mass during polymerization. The polymer was impossible to isolate and test. In contrast the polymer of Example 5, prepared with allyl methacrylate, formed an easy-to-handle viscous liquid, during polymerization.

As can be seen from Table 2, varying the composition of monomers allows for the preparation of copolymers of different molecular weights and glass transition temperatures, which permits modification of the desirable properties of the hair styling compositions formulated with the copolymers.

Examples of Block Copolymers for Hair Styling Aid Formulations

A hair fixative resin should also encompass a number of subjective and objective properties such as curl ease of formulation, sprayability, feel on the hair, washability, curl retention, fast drying and low tack, compatibility with ancillary formulation additives, etc.

The following examples show that blocky/branched copolymers were prepared to demonstrate that, hair fixative polymers with superior performing properties can be obtained by varying the hydrophilic and hydrophobic character of the A and B blocks.

TABLE 4

|  |  | Monomer Composition | | | | |
|---|---|---|---|---|---|---|
|  |  | A-block | B-block | Total Batch | | |
| Example | Monomer | (g) | (g) | (g) | phm | Observations |
| 7 | MAA | 531.00 | 511.50 | 1042.50 | 34.75 | Forms clear |
|  | AA | 144.00 | 576.00 | 720.00 | 24.00 | Solution At |
|  | n-BA | 1200.00 |  | 1200.00 | 40.00 | pH = 9.93 |
|  | All MA | 25.00 | 12.50 | 37.50 | 1.25 |  |
|  | Lup - 11 | 52.50 | 0.00 | 52.50 | 1.75 |  |
|  | IPA/H2O |  |  | 3000.00 | 100.00 |  |
| 8 | MAA | 531.00 | 511.50 | 1042.50 | 34.75 | Forms clear |
|  | AA | 720.00 | 0.00 | 720.00 | 24.00 | Solution At |
|  | n-BA | 1200.00 |  | 1200.00 | 40.00 | pH = 5.44 |
|  | All MA | 25.00 | 12.50 | 37.50 | 1.25 |  |
|  | Lup - 11 | 52.50 | 0.00 | 52.50 | 1.75 |  |
|  | IPA/H2O |  |  | 3000.00 | 100.00 |  |
| 9 | MAA | 531.00 | 511.50 | 1042.50 | 34.75 | Forms clear |
|  | AA | 576.00 | 144.00 | 720.00 | 24.00 | Solution |
|  | n-BA | 1200.00 |  | 1200.00 | 40.00 | At pH = 8.2 |
|  | All MA | 25.00 | 12.50 | 37.50 | 1.25 |  |
|  | Lup - 11 | 52.50 | 0.00 | 52.50 | 1.75 |  |
|  | IPA/H2O |  |  | 3000.00 | 100.00 |  |
| 10 | MAA | 209.00 | 833.50 | 1042.50 | 48.75 | Forms clear |
|  | AA | 720.00 | 0.00 | 720.00 | 10.00 | Solution |
|  | n-BA | 1200.00 |  | 1200.00 | 50.00 | At pH = 5.5 |
|  | All MA | 25.00 | 12.50 | 37.50 | 1.25 |  |
|  | Lup - 11 | 52.50 | 0.00 | 52.50 | 1.75 |  |
|  | IPA/H2O |  |  | 3000.00 | 100.00 |  |

Note that by altering the hydrophilic hydrophobic balance of the A-block polymers soluble within a range of pH were made. Polymers that dissolve at relatively lower pH such as the polymers from Examples 8 and 10 are desired for hair fixatives. Polymers that dissolve at higher pH would be more suitable for formulations where high pH is a benefit, i.e., depilatories, medicated creams, etc.

Sprayability: Hair spray products are typically formulated in hydroalcoholic formulations. It is required that hair fixative resin produces a low viscosity formulations that can be aesthetically delivered in the form a fine spray. The data on Table 5 shows that the Block/Branched copolymers of examples 7, 8, and 9 have better sprayability than current art.

Hair Feel: The tactile feel that the hair acquires after been coated with a fixative resin is extremely important. Current polymers tend to leave the hair raspy, dry, gummy, grease, etc. The data in Table 5 shows that the copolymers 7, 8, and 9 have superior feel characteristics. They leave the hair soft and natural.

Tack: Most current fixative polymers tend to absorb moisture and therefore become tacky. Note that copolymers 7, 8, and 9 exhibit low tack.

Flake-off: Fixative polymers, after drying on hair, exhibit high levels of flakes after combing, giving the hair a dandruff-like appearance. Copolymers 7, 8, and 9 exhibit the lowest levels of flaking.

TABLE 5

(Subjective properties were evaluated directly on hair tresses. 1 = worst, 10 = best)

| Polymer | Hair Feel | Tack | Flake off | Sprayability | % Set Retention 1 hr, 90% RH |
|---|---|---|---|---|---|
| PVP,* | 3 | 2 | 2 | 1 | 30.00 |
| Amphomer** | 2 | 3 | 8 | 2 | 80.00 |
| Lovocryl L73*** | 2 | 3 | 8 | 2 | 50.00 |
| Luv VA73 | 4 | 6 | 6 | 3 | 30.00 |

TABLE 5-continued (Subjective properties were evaluated directly on hair tresses.
1 = worst, 10 = best)

| Polymer | Hair Feel | Tack | Flake off | Sprayability | % Set Retention 1 hr, 90% RH |
|---|---|---|---|---|---|
| Luv Hold. | 4 | 6 | 6 | 3 | 30.00 |
| Example 7 | 6 | 5 | 8 | 6 | 30.00 |
| Example 8 | 6 | 5 | 8 | 8 | 90.00 |
| Example 9 | 5 | 5 | 8 | 7 | 84.00 |
| Example 10 | 5 | 5 | 3 | 3 | 100.00 |

*PVP is polyvinyl pyrrolidone
**Amphomer is a polymer sold by the M. H. Starch Co.
***Lovocryl, Luv are trade names for polymers sold by BASF An important performance property that a hair fixative polymer must also have, is its ability to hold a hairstyle in place at relatively high humidity, i.e., Curl Retention. The curl retention ability of the copolymers of this invention was measured and compared against a number of current hair fixative polymers.

Curl Retention Protocol: 0.05 grams of resin dissolved in a hydroalcoholic solution was applied and smeared on clean, 2 grams, 6 in, hair swatches. The swatches were rolled over salon rollers, dried and conditioned overnight. The swatches were mounted inside a humidity chamber at 80° F., and 90% of relative humidity.

The curl retention was recorded as a function of time and calculated as:

$$(L-L(t)/L-L(o)) \times 100 = \text{curl retention \%}$$

Where:

L=length of hair fully extended, L(o)=length of hair before exposure to high humidity, L(t)=length of hair after exposure at time(t).

As shown in Table 5, the curl retention ability of the blocky-branched copolymers of Examples 8, 9, and 10 was superior to most current fixative polymers.

Copolymer examples 11 and 12, in Table 6, show block copolymers where the A-Block includes 2 ethylhexacrylate (2-EHA) and ethylacrylate (EA), respectively.

TABLE 6

| | | Monomer Composition | | | | |
|---|---|---|---|---|---|---|
| Exam-ple | Ingre-dients | A-Block (g) | B-Block (g) | Total Batch (g) | (phm) | Observations |
| 11 | MAA | 446.00 | | 1316.50 | 58.75 | Soluble in water at pH = 8.02 |
| | 2-EHA | 1200.00 | | 1200.00 | 40.00 | |
| | All MA | 25.00 | 12.50 | 37.50 | 1.25 | |
| | Lup-11 | | | 30.00 | 1.00 | |
| | IPA/H₂O | | | 3000.00 | 100.00 | |
| 12 | MAA | 446.00 | 1316.50 | 1762.50 | 58.75 | Soluble in water at pH = 6.61 |
| | EA | 1200.00 | | 1200.00 | 40.00 | |
| | All MA | 25.00 | 12.50 | 37.50 | 1.25 | |

TABLE 6-continued

| | | Monomer Composition | | | | |
|---|---|---|---|---|---|---|
| Exam-ple | Ingre-dients | A-Block (g) | B-Block (g) | Total Batch (g) | (phm) | Observations |
| | Lup-11 | | | 21.00 | 1.00 | |
| | IPA/H₂O | | | 3000.00 | 100.00 | |

Low VOC hair styling compositions were prepared using the copolymers of Example 2. The compositions included 3–5 weight percent of a resin containing 60% weight percent of one of the copolymers of Table 2, a solvent system, comprising ethanol and water, and a surfactant, AMP-95. All the compositions were formulated to 50% by weight VOC's. Table 7 lists the components of compositions and summarizes the subjective assessments. The compositions show improved performance over conventional, widely used hair styling formulations. The improved performance is seen in one or more of the following attributes: style retention at high humidity, natural feel, combability, reduced flaking, good styleability and restyleability.

TABLE 7

Hair Styling Compositions Containing 50% VOC

| Ingredient | % wt | Comments: |
|---|---|---|
| Composition A | | |
| Polymer of Example 1 | 3.00 | Feel of hair is slick initially then it |
| Ethanol | 50.00 | has a very touchable feel when |
| Amp 95* | 0.30 | completely dry. |
| Deionized water | 46.70 | |
| Composition B | | |
| Polymer of Example 2 | 5.00 | Same as for composition A. |
| Ethanol | 50.00 | |
| Amp 95 | 0.50 | |
| Deionized water | 44.50 | |
| Composition C | | |
| Polymer of Example 3 | 3.00 | Feel of hair is slick initially then |
| Ethanol | 50.00 | becomes touchable when dry. |
| Amp 95 | 0.17 | Humidity resistance is greater than |
| Deionized water | 46.83 | for conventional PVP and PVP/vinyl acetate in alcohol formulations. |
| Composition D | | |
| Polymer of Example 3 | 5.00 | Same as for Composition C. |
| Ethanol | 50.00 | |
| Amp 95 | 0.29 | |
| Deionized water | 44.71 | |

*AMP 95 is amino methyl propanol, 95% wt. in water

Swatches of hair were sprayed or applied with the hair styling compositions in Table 7. The swatches were evaluated for humidity resistance, expressed in terms of percentage droop (in relation to a fully extended swatch of hair). Subjective assessments of natural feel, combability, resistance to flaking, and restylability/stylability were also made, on a 1 to 10 scale, 10 being the optimum. Table 8 summarizes these characteristics for the four hair styling compositions in Table 7.

TABLE 8

Hair Styling Properties of Compositions Including the Copolymer

| Composition | Humidity Resistance | Natural Feel | Combability | Flaking | Restylability Stylability |
|---|---|---|---|---|---|
| A | 30 min - 76% curl drop, 45 min - curl drop | 6 | 9 | 8 | 7 |
| B | 30 min - 92% curl drop, 1 hr. - curl drop | 6 | 9 | 7 | 7 |
| C | 7 hrs. - 88% curl drop, 24 hrs. - full droop | 6 | 9 | 10 | 8 |
| D | 46 hrs - 88% curl drop, 72 hrs. - full droop | 6 | 9 | 8 | 8 |

As seen from Table 8, all of the compositions exhibited better than average natural, feel, combability, resistance to flaking, and stylability/ restylability characteristics. For hair styling compositions employing the same (composition A and B or C and D), these characteristics were rated equally for compositions having lower resin concentration (3%) and those with a higher resin concentration (5%), with the exception of resistance to flaking, which showed a marginal improvement at lower resin concentrations. Humidity resistance was greater at higher resin concentrations.

Examples of Reduced VOC Aerosol Hair Fixative Formulations

Example E. 55% VOC Aerosol Hair Spray Using Dimethyl Ether

| Item No. | Ingredient | Wt % |
|---|---|---|
| 1 | SD 40–200 Alcohol | 25.0 |
| 2 | Water | 35.0 |
| 3 | Example 5 | 8.0 |
| 4. | AMP-95 | 2.0 |
| 5 | Dimethyl Ether | 30.0 |

Items 1 thru 4 added and mixed in a container until a clear solution is obtained. This formulation was placed in an aerosol hair spray can. The can was capped with a standard aerosol actuator. Item 5 was pressure charged into the can. Upon discharging the product, the spray pattern was excellent, a very fine aerosol mist was obtained.

Example F. 55% VOC Aerosol Hair Spray Using 152A Propellant

| Item No. | Ingredient | Wt % |
|---|---|---|
| 1 | SD 40–200 Alcohol | 55.0 |
| 2 | Polymer of Example 5 | 8.0 |
| 3 | AMP-95 | 2.0 |
| 4 | Dymel 152A | 35.0 |

Items 1 thru 4 were added and mixed in a container until a clear solution is obtained. This formulation was placed in an aerosol hair spray can. The can was capped with a standard aerosol actuator. Item 5 was pressure charged into the can. Upon discharging the product, the spray pattern was excellent; a very fine aerosol mist was obtained.

Example G. Styling Mousse

| Item No. | Ingredient | Wt % |
|---|---|---|
| 1 | Water | 81.0 |
| 2 | Polymer of Example 5 | 3.5 |
| 3 | Emulphor on-870 | 0.5 |
| 4 | Propellant A-46 | 15.0 |

Item 1 thru 3 were added and mixed in a container until a clear solution is obtained. This formulation was placed in an aerosol mousse can. The can was capped with a standard mousse actuator. Item 4 was pressure charged into the can. Upon discharging the product, a thick and creamy foam was obtained.

The following examples are intended to illustrate the range of uses for the film forming copolymers of this invention:
Ultrasonic Diagnosis Gel
0.5% Carbomer thickener
2.0% Polymer of Example 7
0.25% of NaOH
5.0% of glycerol to 100% with water+preservative
Ointment with Zinc Oxide
1.2% Polymer of Example 10
1.0% triethanolamine
14.0% of zinc oxide to 100% with water+preservative
Furniture Polish
1.0% Polymer of Example 10
5.0% silicone oil emulsions (30% strength)
3.0% carnauba wax emulsion (20% strength) to 100% with water
Domestic Cleaning Agent
1.5% Polymer of Example 10
1.3% triethanolamine
10.0% isopropyl alcohol
10.0% nonylphenol+10 moles of ethylene oxide to 100% water
Water-In-Oil Cream
0.5% Polymer of Example 10
0.1% monoethanolamine
3.5% diglycerol sesquiissostearate
10.0% paraffin wax
5.0% cetyl alcohol
2.2% microwax
0.2% perfume oil to 100% water+perservative
After Shave Gel
1.1% Polymer of Example 10
0.4% monoethanolamine
35.0% ethyl alcohol
0.1% menthol to 100% with water+preservative Hair Shampoo
0.5% Polymer of Example 10
0.6% triethanolamine
12.0% coconut oil alcohol+10 moles of ethylene oxide
0.1% perfume oil to 100% of water+preservative
Hand Sanitizer
1.0% Polymer of Example 10
65.0% ethyl alcohol
1.5% carbopol
1.4% triethanolamine
0.1% perfume oil to 100% with water+preservative
Liquid Oil-In-Water Emulsion
0.5% Polymer of Example 10
0.2% NaOH
5.0% isopropyl palmitate
5.0% paraffin oil
5.1% diglycerol stearate+4 moles of ethylene oxide
0.1% perfume oil to 100% with water+preservative
Oil-In-Water Cream
0.7% Polymer of Example 10
0.6% AMP-95
5.0% petrolatum
5.2% soybean oil
3.0% glycerol monostearate
3.0% tri-stearyl tetraglycol ether ortho-phosphoric acid to 100% with water+preservative
Liquid Water-In-Oil Emulsion
0.5% Polymer of Example 10
0.6% ammonium hydroxide (10% strength)
3.0% hydrogenated castor oil+7 moles of ethylene oxide
2.0% polyglyceryl-2 sesquiisostearate
1.0% beeswax
1.0% mineral oil
0.5% magnesium stearate
0.5% aluminum montanate
10.0% isopropyl palmitate
15.% perhydrosqualene to 100% with preservative+water The hair styling compositions of this invention, containing the unique block copolymers discussed above, have particularly good wicking or flow on the hair. The superior flow on the hair also has a leveling effect that may increase shine in certain conditions, such as in the damaged hair. This property was demonstrated by the below described Hair Wicking Test Procedure.

Hair Wicking Test Procedure

Equipment Used:
  Mettler AE 260 Delta Range® Balance
  IBM Compatible PC
  Fixture for attaching hair to balance pan
  Shelf for holding solutions
Software Used:
  Mettler BalanceLink Version 2.0
  ®Mettler-Toledo AG 1994
  CH-8606 Greifensee, Switzerland
Data Handling:
  Command to send every 10 seconds
  2400 Baud Rate, COM1 Serial Port
  Data normalized by hair weight
Accessories:
  Tubes for holding hair tresses (120 +/−0.5 mm length)(7.5 mm diameter)
  Tubes are split lengthwise to allow loading of double hair tresses
  100 mL Pyrex no. 1000 beaker (47 mm diameter)

Test Specimens:
  Crimped metal band European brown hair 180 mm long
  Double tresses used to produce hair volume (to fill the tube)
  Experimental hair solutions
Test Procedure:
Hair tresses are numbered and weighed before testing. Tresses are loaded into the tube so that the end of the hair is even with the bottom of the tube. A clip is then attached to the hair. Balance is tared to zero with no hair loaded. Hair is loaded to fixture attached to balance pan and balance retared. Hair tresses are removed from balance and 60 grams of experimental solution is placed in a 100 mL beaker on a tray above the balance pan. File name is created in the software and data acquisition started. After first point appears on screen, hair tress is loaded onto balance stand fixture so plastic tube with hair is immersed in solution. Data readings were taken every 10 seconds until uptake has reached steady state.

Figure 2:
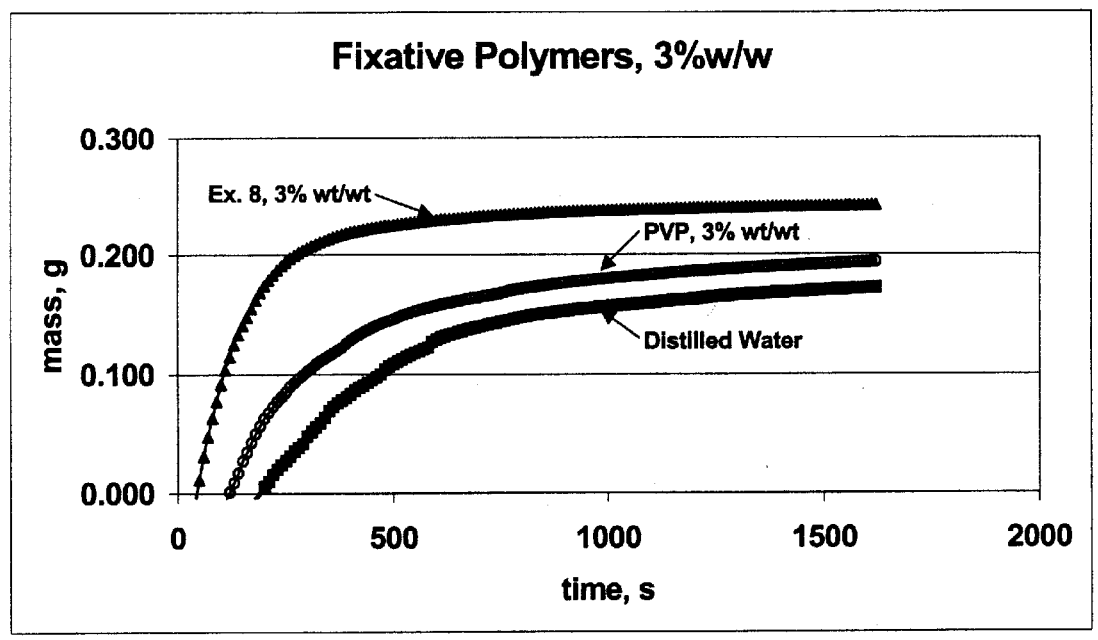
FIG. 2 shows the uptake by the hair of the 3% solution of the polymer of Example 8 and of PVP.

Conclusions of Wicking Test:
The above procedure was carried out using distilled water and 1%, 3% and 5% aqueous solutions of the copolymer of Example 8 to determine the weight of water and of the polymeric solutions that were taken up by the tress. FIG. 1 shows that the uptake of the polymeric solutions is much quicker and much greater than of water. FIG. 2 shows similar data comparing the uptake of the 3% solution of the polymer of Example 8 and of PVP. The uptake of the solution of Example 8 is substantially quicker and about 30% greater than that of the PVP solution.

Figure 3:
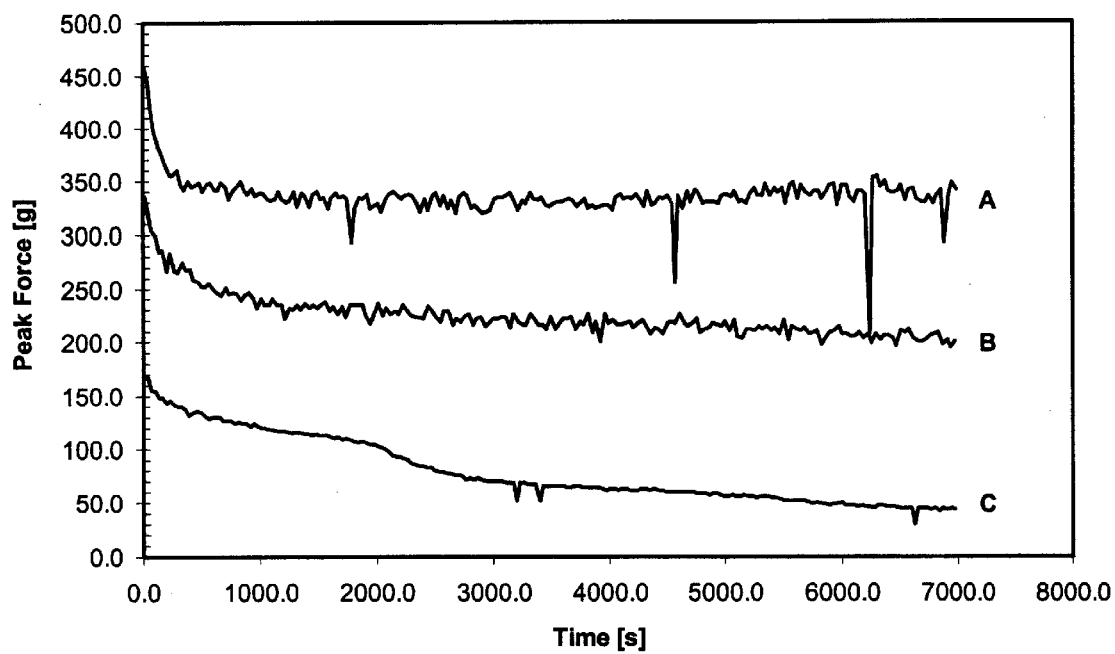
FIGS. 3, 4 and 5 show the force required to deform the hair loops at various stages of the test.
Figure 4:
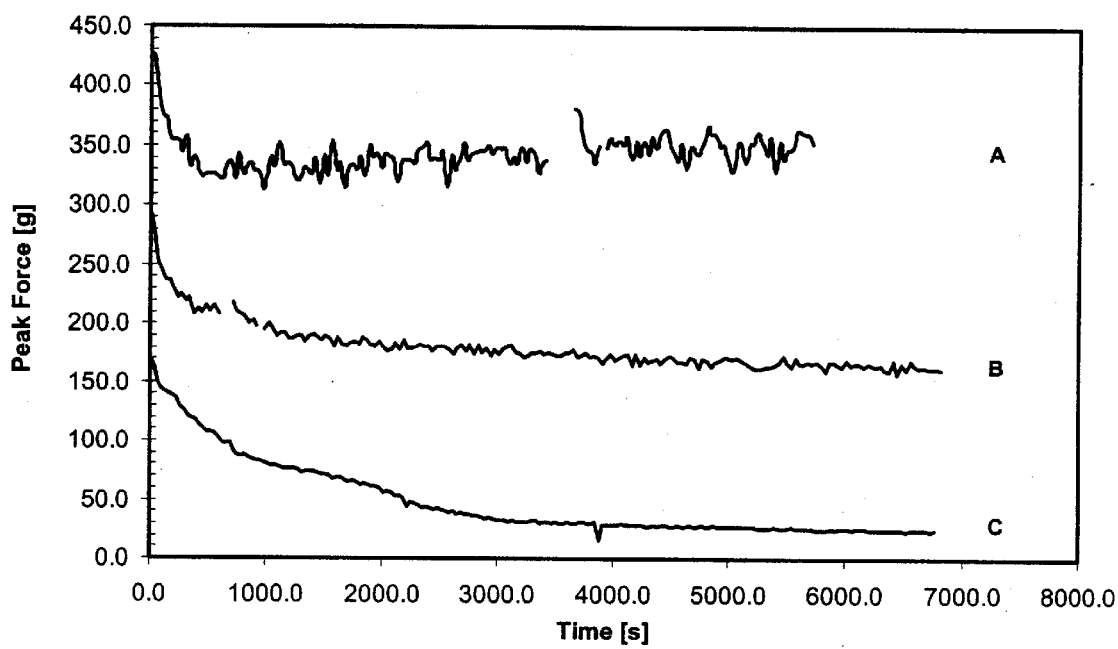
Figure 5:
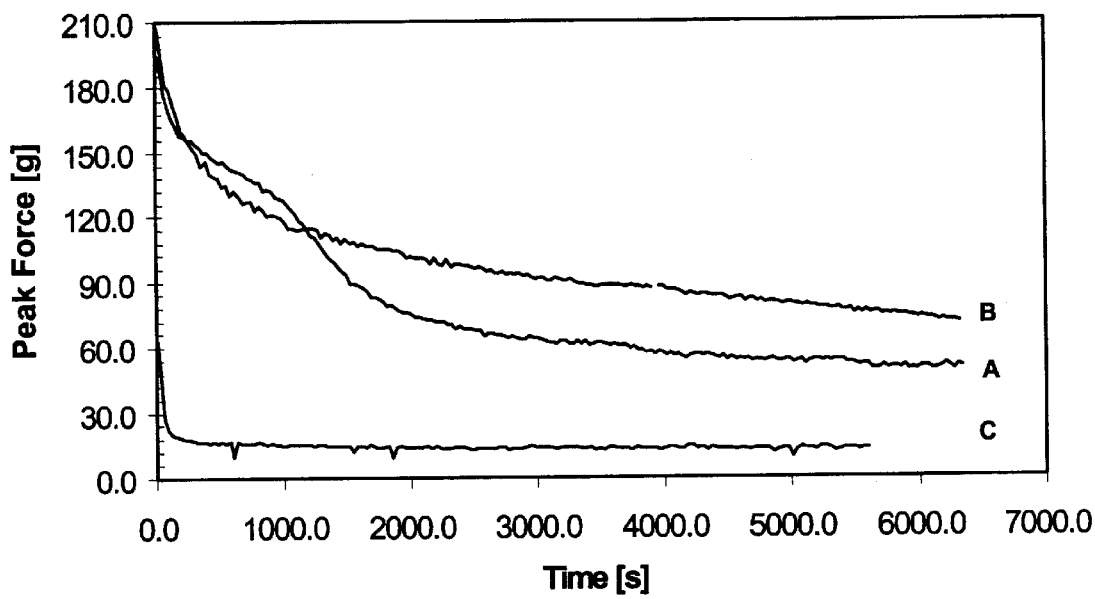

Hair styling formulations that employ existing polymers generally have deficiencies in restylability, especially in high humidity. The block copolymers of this invention perform particularly well under such challenging conditions. This unexpectedly good performance was demonstrated when compared with PVP and PVP/VA polymers. This is shown in FIGS. 3 to 5 where the data is reported in graph form performed according to the below described procedure.

Restylability Test

A TA Texture Analyzer was placed in the humidity cabinet and the Omega Loop Test was conducted on virgin brown European hair using PVP (polyvinyl pyrrolidone), PVP/VA (polyvinyl pyrrolidone/vinyl acetate) polymers and the polymer of Example 8. This test is based on and is described in greater detail in J. Jachowicz and K. Yao.

The hair loops were prepared with approximately 0.1 gram of 5% aqueous solution of each polymer deposited on wet hair with a micro syringe and allowed to dry before testing. The hair loops were conditioned in an environment that is approximately 50% R.H. and 25° C. The tests were run at 50%, 60%, 70% and 80% R.H. and 25° C. After the tests, the loops were reformed by wetting and rewrapping around a 1" dowel bar. The loops were allowed to condition overnight in the humidity cabinet at 25° C. and at each % R.H. specified above.

A one-hour standard test was conducted, compressing the omega loop 1 mm after initial contact. The computer read an average of 4.8 data points per second. The peak forces of each loop along with the distance the probe traveled to get to the maximum force were calculated and imported to an Excel spreadsheet. The hair loops covered with the aqueous solutions of PVP and PVP/VA polymer have totally broken down while the loop containing the polymer of Example 8 has retained at least some of its fixative nature.

FIGS. 3, 4 and 5 show the force required at the beginning of the test (time-0 sec.) to deform the hair loops by 8 mm (30% deformation of the diameter of the loop) and then each curve shows the decrease in the force required as the test progresses. The deformation of the loop is repeated about 5–6 times per minute and for each loop the maximum force is recorded and plotted in an Excel spreadsheet. The higher the initial force, the crisper the hold. Steep initial drop in the curve means that the bonds of the polymer holding the hair in position are broken down quickly. A gradual decrease in the curve means that the breakdown of the bonds is slow.

FIG. 3 represents the initial test at 70% Relative Humidity (R.H.). Thereafter, the hair loops are restyled as described above and FIG. 4 shows a repeat of the test at 70% R.H. Then the hair loops are restyled again and the test is repeated at 80% R.H.

A repeat of the previous test was done after the hair loops were restyled using water and the teflon coated dowel bar.

The next test was run on the same hair loops, again resulting with water and wrapped around a dowel bar. The humidity was increased to 80% R.H. and the temperature remained at 25° C. The results are shown in FIG. 5.

The curves in FIGS. 3, 4 and 5 show the following information:

1) The PVP resin gives the crispest hold, resin of Example 8 somewhat softer hold and the PVP/VA resin the softest hold for the same amount of polymer.
2) FIGS. 3 and 4 show that both PVP and Example 8 resins have similar restylability patterns at 70% R.H., but PVP/VA resin has a poor restylability property.
3) FIG. 5 shows that when the hair loops are restyled for the second time and at 80% R.H., PVP experiences a substantial loss of restylability compared to the Example 8 resin and PVP/VA is basically no longer restylable.
4) It should be noted that in FIG. 4 the PVP/VA curve shows a slight second inflection around 1500 sec. and in FIG. 5, the PVP curve shows a more pronounced second inflection also around 1500 sec. This indicates that, at that point, the curl (loop) is undone, split apart in the direction tangential to the applied force. This can be easily observed because there are one or more breaks in the loop and the hair separates into several sections with substantial open spaces between these sections. The hair loop containing the Example 8 resin exhibited breaks but retained a complete curl, substantially as in the beginning of the test.

The hair styling composition of this invention, containing the unique block copolymers discussed above, have a unique property of permitting the user to restyle and rejuvenate the hold of the hair hours after the original application without the need to reapply the composition onto the hair. The only requirement is to apply a small amount of water to the hair, such as by spraying and then restyling the hair by the use of a curling iron, blow dryer or curlers and then combing the hair. Other products simply do not provide the ability to restyle the hair hours later without having to apply additional product to the hair. The restylability can be shown by re-evaluating the humidity resistance and by using the Texture Analyzer.

The improved flow onto the hair by aqueous solutions of the copolymer of Example 8 suggests that the hair will appear to have greater volume due to a greater amount of polymer deposited onto the hair. This in turn gives the hair the appearance of being thicker and fuller. This property was demonstrated below by the described Hair Volumizing Procedure.

Hair Volumizing Measurements

Equipment Used:
  Texture Analyzer
  Volumizing Fixture (10 mm ring)
Software Used:
  Version 1.17
  Test Method HVT
Test Parameters:
  2 kg load cell
  Force in grams, distance in mm
  Test speed 4 mm/minute
Sample Preparation:
  Crimped metal band European brown hair 180 mm long;
  Double tresses used to produce hair volume (pull through fixture);
  1 gram of experimental polymer solution applied to hair, allowed to wick into hair, combed through three times with a medium tooth comb and allowed to dry overnight;
  Combed through seven times with medium tooth comb before testing.
Test Procedure:
  Hair was secured in upper fixture by tightening thumb-wheel and the alignment of tress and volumizing ring were checked. Start the test. After the specimen has been pulled free of volumizing ring, the upper crosshead was stopped. Sample was removed and the crosshead was returned to the original starting position. Sample was then reloaded and test procedure restarted until 5 curves had been generated for each tress with each experimental compound. The samples were tested at room temperature.

The following Table 9 illustrates that the polymer of Ex. 8 significantly increases the combing force on the hair which is indicative of the increase of the volume of the hair.

TABLE 9

HAIR VOLUMIZING

Maximum Combing Force, gf
European Brown Virgin Hair

|  | Untreated | Polymer of Ex. 8 |
|---|---|---|
| | Set No. 1 | |
| mean | 22.7 | 140.8 |
| std. dev. | 6.7 | 30 |
| | Set No. 2 | |
| mean | 35.5 | 100.7 |
| std. dev. | 5.1 | 22 |

Humectants are another class of additives that may be employed in the hair formulations of this invention. Humectants are well known in the art and include polyhydric alcohols such as glycerin, sorbitol, propylene glycol and the like. Generally, humectants have a negative impact on hair styling formulations containing prior art polymers in that the curl retention in a high humidity environment is decreased with a humectant. Surprisingly, when the block copolymers of this invention are employed, the resistance to humidity is substantially improved. This effect can be seen in FIG. 6.

The following formulations shown in Table 10 were employed in the below described Curl Retention Tests:

TABLE 10

| INGREDIENT | WEIGHT % | WEIGHT % | WEIGHT % | WEIGHT % |
|---|---|---|---|---|
| Water | 97.00 | 97.00 | 96.16 | 95.16 |
| PVP K-90 | 3.00 | — | — | — |
| PVP/VA 73W | — | 3.00 | — | — |
| AMP-95 (neutralizer) aminomethyl propanol | — | — | 0.84 | 0.84 |
| Copolymer of Ex. 8 pH is 5.9 | — | — | 3.00 | 3.00 |
| Glycerin | — | — | — | 1.00 |
| TOTAL | 100.00 | 100.00 | 100.00 | 100.00 |

The hair samples used in the below described test were 1.6 g, 6-inches in length, 1-inch wide and the flat tress was stapled together.

Each hair styling formulation was applied by dripping 0.8 g of a formulation along the hair tress, combing through and setting the hair tress on a 0.5 inch diameter roller. After setting for about 24 hours at room temperature, the curls were exposed to 90% relative humidity at 25° C.

Curl Retention at 90% R.H. AT 25° C.

The formulation containing the polymer of Example 8 had curl retention of 50% after 8 hours while the hair coated with PVP/VA copolymer had only 15% curl retention after only 2 hours and the sample coated with the formulation containing PVP polymer had only 15% curl retention after 3 hours. Very surprisingly, the formulation containing the polymer of Example 8 and 1% of glycerin had 70% curl retention even after 8 hours in a 90% R.H. environment.

Cleansing Performance: The block copolymers of the present invention also exhibit particular usefulness in shampoo both gel and soap compositions. The shampoo formulations are made to provide good cleansing properties primarily for the purpose of removing oils and dirt from the hair. To attain this capability, it is necessary to add a substantial amount of one or more surfactants, chelating agents and foam stabilizers. The useful surfactants can be anionic, cationic or amphoteric. The anionic surfactant may be an alkyl sulfate, an alkyl ether sulfate, a sulfate ester of an alkylphenoxy polyoxyethylene ethanol, an alpha-olefin sulfonate, a beta-alkoxy alkane sulfonate, an alkyl aryl sulfonate, an alkyl carbonate, a sulfoxuccinate, an alkyl ether sulfosuccinate, a sacristan, an octoxynol phosphate, a nonoxynol phosphate, a taurate, a fatty tauride, a sulfated monoglyceride, a fatty acid polyoxyethylene sulfate, an isethienate and mixtures thereof. The specific formulations may vary greatly from one brand to another but all shampoos generally contain these ingredients. To improve the cleaning capability, either stronger surfactants are used or the amount of the surfactants is increased. This, however, often causes irritation to the skin, especially in people who have greater sensitivity to chemicals in general. For this reason, shampoos have been formulated with milder types of surfactants or a lesser amount of the surfactants is being used. But this results with a shampoo that often has inadequate cleaning capability. The block copolymers of the present invention unexpectedly improve the cleaning efficiency and effectiveness of a shampoo formulation. This enables the formulator to use lesser amounts of the surfactants and to use milder surfactants but still maintain an unusually high degree of oil and dirt removal capability. For example, regular strength shampoos will usually incorporate more than 12 parts of 1 or more surfactants per 100 parts of the formulation and often 14 and more parts. The milder types of shampoos will generally use up to 12 parts and often less, such as between 8 and 12 parts (actives) per 100 parts of the formulation. Thus a formulator may avoid having to use harsher surfactants and smaller amounts of surfactants to prepare a shampoo that is very mild and non-irritating to the skin yet exhibit exceptionally high ability to remove oils and dirt from the hair. In other words, these block copolymers increase the effectiveness of surfactants used in hair shampoos, Using the Rubine Dye Test, as discussed in U.S. Pat. No. 3,769,398, Table 11 below shows the cleaning improvement resulted by incorporating the copolymer of Example 8 in a shampoo formulation.

TABLE 11

| INCI-CTFA Name | Weight % A | Weight % B | Function | Trade Name (Supplier) |
|---|---|---|---|---|
| Deionized Water | 62.6 | 62.6 | Diluent | D.I. Water |
| Acrylates/C10–30 Acrylate Crosspolymer | 0.75 | 0.75 | Rheology Modifier | ETD 2020 (B F Goodrich) |
| Aminomethyl Propanol | 0.25 | 0.25 | Neutralizer | AMP 95 (Angus) |
| Sodium Laureth Sulfate (28%, 2 mole EO) | 14 | 12 | Surfactant | Texapon NSO (Henkel) |
| Decyl Glucoside (50%) | 12 | 12 | Surfactant | Plantacare 2000 (Henkel) |
| Cocoamphoacetate 80% | 6.5 | 6.5 | Surfactant | Empigen CDR 90 (Albright & Wilson) |
| Tetrasodium EDTA | 0.2 | 0.2 | Chelating agent | Trilon B liquid (BASF) |
| Disodium Laureth Sulfosuccinate 40% | 2 | 2 | Surfactant | Setacin 103 (Zschimmer & Schwarz) |
| Phenoxyethanol (and) Methylparaben (and) Ethylparaben (and) Propylparaben (and) Butylparaben | 0.5 | 0.5 | Preservative | Phenonip (Nipa Laboratories) |
| Soyamide DEA | 1.2 | 1.2 | Foam Stabilizer | Purton SFD (Zschimmer & Schwarz) |
| Copolymer of Ex. 8 | 0 | 2 | Film former | (B F Goodrich) |

Formulation A which did not contain the copolymer of Example 8 had a cleaning rating of 6 while Formulation B which contained 2% of the copolymer of Example 8 had a cleaning rating of 8.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A film forming block copolymer formed in the presence of a free radical initiator from:

(A) a polyfunctional monomeric chain extender having at least two functional groups, the reactivity of one functional group being substantially higher than that of the other functional group, wherein the polyfunctional chain extender has the formula:

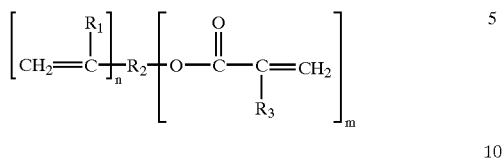

where n and m independently are integers from 1 to 4; $R_1$ and $R_3$ independently are H or alkyl; and $R_2$ is alkylene, cycloalkylene, arylene, $-(CH_2-CH_2-O)_p-$ where p=1 to 50, $-CH_2(CH_3)-CH_2-O)_p-$ where p=1 to 50, amido, ester, or combinations thereof;

(B1) a first ethylenically unsaturated monomer or monomers which copolymerize in the presence of a free radical initiator preferentially with the functional group of the polyfunctional chain extender which has a higher reactivity to form a first block, wherein the first ethylenically unsaturated monomer comprises one or more of:

(1) acrylic acid or methacrylic acid; fumaric acid, itaconic acid or aconitic acid; maleic anhydride; and
(2) esters or amides respectively having the formula:

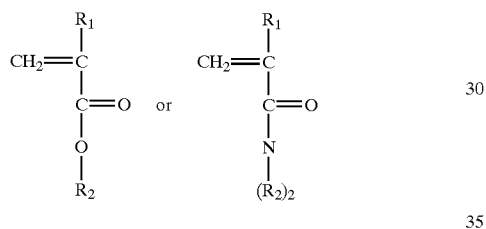

wherein $R_1$ is $-H$, $-CH_3$, or $-CH_2CH_3$; and $R_2$ is an aliphatic hydrocarbon functional group having at least one carbon, a polynuclear aromatic hydrocarbon group, an alkylaryl wherein the alkyl has one or more carbons, a haloalkyl having 4 or more carbons, a polyalkyleneoxy group wherein said alkylene is propylene or higher alkylene and there is at least 1 alkyleneoxy unit per hydrophobic moiety; α-olefins; vinyl alkylates; vinyl alkyl ethers; N-vinyl amides; or combinations thereof, and (B2) a second ethylenically unsaturated monomer or monomers which copolymerizes in the presence of a free radical initiator with the functional group of the polyfunctional chain extender which has the lesser reactivity to form a second block, wherein the second ethylenically unsaturated monomer comprises one or more of:

(1) an ethylenically unsaturated amide having the formula:

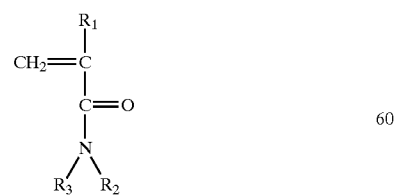

where $R_1$ is $-H$, $-CH_3$, $-CH_2-CH_3$, branched or linear alkyl, aryl, or cycloalkyl; and $R_2$ and $R_3$ independently are $-H$, $-CH_3$, $-CH_2-CH_3$, branched alkyl, linear alkyl, aryl, cycloalkyl, acid or salt functional, amino functional, or quaternized groups, or combinations thereof; and (2) ethylenically unsaturated carboxylic acids having at least one of the following formulas:

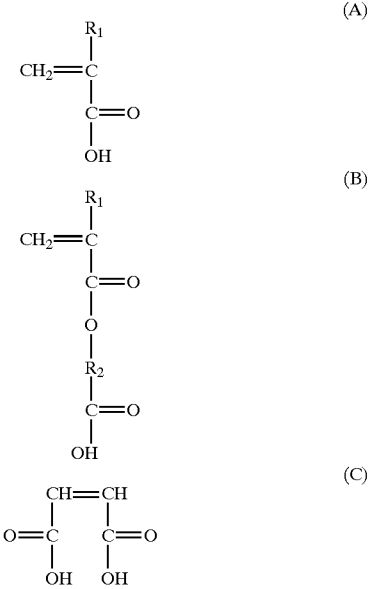

where $R_1$ is $-H$, $-CH_3$, or $-CH_2CH_3$; and $R_2$ is $-[CH_2-]_n$ where n is an integer from 1 to 40, linear or branched alkylene, cycloalkylene, arylene, polyethylene oxide; or polypropylene oxide; methacrylic acid, crotonic acid, itaconic acid and fumaric acid; half esters of maleic and fumaric acids; or combinations thereof; and wherein said (A) polyfunctional monomeric chain extender comprises from about 0.005 to 2 mole percent of the total monomers and substantially does not itself polymerize; said (B1) first ethylenically unsaturated monomer comprises from about 5 to about 95 mole percent of the total monomers; and said (B2) second ethylenically unsaturated monomer comprises from about 5 to about 70 mole percent of the total monomers; wherein said block copolymer has an average molecular weight up to 1,000,000, said first block is more hydrophobic than said second block, said first block has a molecular weight of at least 10,000 and a glass transition temperature of about 30° C. or less, and said second block has a molecular weight of at least 1,000 and glass transition temperature of greater than 30° C., wherein said film forming block copolymer has substantially the following structure:

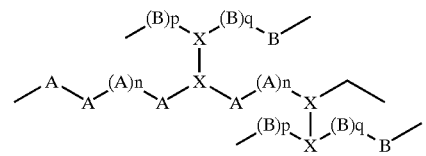

wherein A represents a block obtained from the first ethylenically unsaturated monomer or monomers, B represents the block obtained from the second ethylenically unsaturated monomer or monomers and X represents the unit obtained from the polyfunctional monomeric chain extender; n represents the degree of polymerization of the A-block which is larger than 100 and q and p represents the degree of polymerization of the B-block which is larger than 100 such that either q or p can be zero but not both at the same time.

2. A hair styling composition containing a film forming block copolymer formed in the presence of a free radical initiator from:

(A) a polyfunctional monomeric chain extender having at least two functional groups, the reactivity of one functional group being substantially higher than that of the other functional group, wherein the polyfunctional chain extender has the formula:

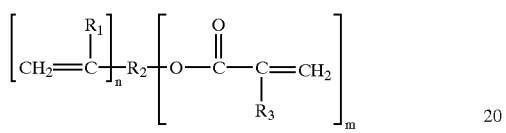

where n and m independently are integers from 1 to 4; $R_1$ and $R_3$ independently are H or alkyl; and $R_2$ is alkylene, cycloalkylene, arylene, —$(CH_2—CH_2—O)_p$— where p=1 to 50, —$CH_2(CH_3)$—$CH_2$—$O)_p$— where p=1 to 50, amido, ester, or combinations thereof;

(B1) a first ethylenically unsaturated monomer or monomers which copolymerize in the presence of a free radical initiator preferentially with the functional group of the polyfunctional chain extender which has a higher reactivity to form a first block, wherein the first ethylenically unsaturated monomer comprises one or more of:

(1) acrylic acid or methacrylic acid; fumaric acid, itaconic acid or aconitic acid; maleic anhydride; and (2) esters or amides respectively having the formula:

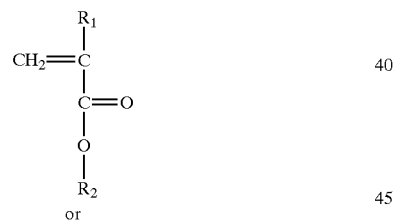

or

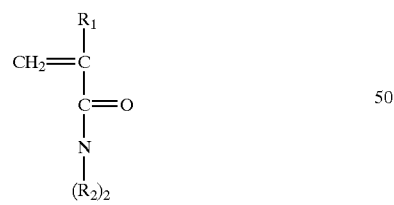

wherein $R_1$ is —H, —$CH_3$, or —$CH_2CH_3$; and $R_2$ is an aliphatic hydrocarbon functional group having at least one carbon, a polynuclear aromatic hydrocarbon group, an alkylaryl wherein the alkyl has one or more carbons, a haloalkyl having 4 or more carbons, a polyalkyleneoxy group wherein said alkylene is propylene or higher alkylene and there is at least 1 alkyleneoxy unit per hydrophobic moiety; α-olefins; vinyl alkylates; vinyl alkyl ethers; N-vinyl amides; or combinations thereof, and (B2) a second ethylenically unsaturated monomer or monomers which copolymerizes in the presence of a free radical initiator with the functional group of the polyfunctional chain extender which has the lesser reactivity to form a second block, wherein the second ethylenically unsaturated monomer comprises one or more of:

(1) an ethylenically unsaturated amide having the formula:

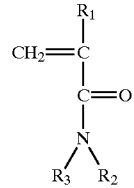

where $R_1$ is —H, —$CH_3$, —$CH_2$—$CH_3$, branched or linear alkyl, aryl, or cycloalkyl; and $R_2$ and $R_3$ independently are —H, —$CH_3$, —$CH_2$—$CH_3$, branched alkyl, linear alkyl, aryl, cycloalkyl, acid or salt functional, amino functional, or quaternized groups, or combinations thereof; and (2) ethylenically unsaturated carboxylic acids having at least one of the following formulas:

(A)

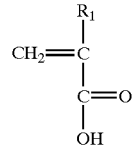

(B)

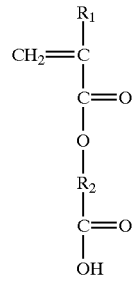

(C)

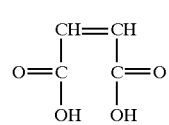

where $R_1$ is —H, —$CH_3$, or —$CH_2CH_3$; and $R_2$ is —$[CH_2—]_n$ where n is an integer from 1 to 40, linear or branched alkylene, cycloalkylene, arylene, polyethylene oxide; or polypropylene oxide; methacrylic acid, crotonic acid, itaconic acid and fumaric acid; half esters of maleic and fumaric acids; or combinations thereof; and wherein said (A) polyfunctional monomeric chain extender comprises from about 0.005 to 2 mole percent of the total monomers and substantially does not itself polymerize; said (B1) first ethylenically unsaturated monomer comprises from about 5 to about 95 mole percent of the total monomers; and said (B2) second ethylenically unsaturated monomer comprises from about 5 to about 70 mole percent of the total monomers; wherein said block copolymer has an average molecular weight up to 1,000,000, said first block is more hydrophobic than said second block, said first block has a molecular weight of at least 10,000 and a glass transition temperature of about 30° C. or less, and said second block has a molecular weight of at least 1,000 and glass transition temperature of greater than 30° C., wherein said film forming block copolymer as substantially the following structure:

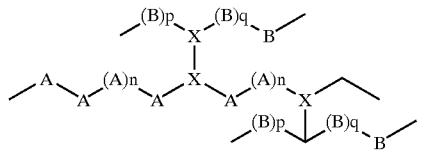

wherein A represents a block obtained from the first ethylenically unsaturated monomer or monomers, B represents he block obtained from the second ethylenically unsaturated monomer or monomers and X represents the unit obtained from the polyfunctional monomeric chain extender; n represents the degree of polymerization of the A-block which is larger than 100 and q and p represents the degree of polymerization of the B-block which is larger than 100 such that either q or p can be zero but not both at the same time.

3. A hair shampoo composition containing a film forming block copolymer of claim 1.

4. The copolymer of claim 1, wherein:
the polyfunctional monomer comprises from 0.1 to 1.5 mole percent of the total monomers;
the first ethylenically unsaturated monomer comprises from 5 to 50 mole percent of the total monomers; and
the second ethylenically unsaturated monomer comprises from 10 to 70 mole percent of the monomers.

5. The copolymer of claim 1, wherein the first block has a molecular weight of 10,000 to 100,000.

6. The copolymer of claim 1, wherein the second block has a molecular weight of 1,000 to 100,000.

7. The copolymer of claim 1, wherein the first ethylenically unsaturated monomer is an acrylamide or methacrylamide selected from the group consisting of N-ethyl acrylamide, N-tertiary-octyl acrylamide, N-decyl acrylamide, N-dodecyl acrylamide, N-ethyl methacrylamide, N-tertiary octyl methacrylamide, N-decyl methacrylamide, N-dodecyl methacrylamide, and combinations thereof.

8. The copolymer of claim 1, wherein the first ethylenically unsaturated monomer is selected from the group consisting of alkyl esters of acrylic acid, methacrylic acid, mono or di-alkyl acrylamides, and mono or di-alkyl methacrylamides, wherein the alkyl has from 2 to 8 carbon atoms; and combinations thereof.

9. The copolymer of claim 1, wherein the first ethylenically unsaturated monomer is selected from the group consisting of n-butyl acrylate, t-butyl acrylate, ethyl acrylate, 2-hexyl acrylate, and combinations thereof.

10. The copolymer of claim 1, wherein the polyfunctional monomer is selected from the group consisting of allyl methacrylate, allyl acrylate, vinyl methacrylate, vinyl acrylate, vinyl acrylamide, vinyl methacrylamide, allyl methacrylamide, allyl acrylamide, and mixtures thereof.

11. The copolymer of claim 1, wherein the reactivity of the first functional group is from about three to ten times more than the reactivity of the second functional group, allyl or vinyl.

12. The copolymer of claim 1, wherein the first functional group is an allyl vinyl group and wherein the second functional group is selected from the group consisting of methacrylic and acrylic functional groups.

13. The copolymer of claim 1, wherein the second ethylenically unsaturated monomer is sufficiently water soluble or dispersible to form at least a 20 weight percent solution when dissolved in water.

14. The copolymer of claim 1, wherein the second ethylenically unsaturated monomer is an ethylenically unsaturated amide selected from the group consisting of acrylamide, methacrylamide and fumaramide, and their N-substituted derivatives, such as 2-acrylamido-2-methylpropane sulfonic acid, N-(dimethylaminomethyl) acrylamide; N-(trimethylammonium-methyl)acrylamide chloride; and N-(trimethylammoniumpropyl)-methacrylamide chloride.

15. The copolymer of claim 1, wherein the second ethylenically unsaturated monomer is selected from the group consisting of 2-aminoethyl methacrylate; N,N-dimethyl-aminoethyl methacrylate; N,N-dimethyl aminoethyl acrylate; 2-tert-butyl aminoethyl methacrylate; 2-trimethylammonium ethylmethacrylate chloride; 2-trimethylammonium ethylacrylate chloride; vinyl amines, such as vinyl pyridine and vinyl morpholine; diallyl amines; and diallyl ammonium compounds, such as diallyl dimethyl ammonium chloride.

16. The copolymer of claim 1, wherein the second ethylenically unsaturated monomer is selected from the group consisting of acrylic acid, methacrylic acid, crotonic acid, itaconic acid, maleic acid, fumaric acid, $C_1$–$C_4$ alkyl half esters of maleic and fumaric acids, and combinations thereof.

17. The copolymer of claim 1, wherein the polyfunctional monomer is allyl methacrylate, the first ethylenically unsaturated monomer is a mixture of n-butyl acrylate and (meth) acrylic acid and the second ethylenically unsaturated monomer is selected from the group consisting of acrylic acid, methacrylic acid and mixtures thereof.

18. The hair styling composition of claim 2, further including at least one of the following materials:
0 to 25 weight percent of an emulsifier;
0.05 to 99% solvents;
0.05 to 10% rheology modifiers;
0.05 to 5% neutralizing agents;
0–60 weight percent of a liquid propellant or gas; and,
0–1% of a surfactant.

19. A hair styling composition including:
from about 0.5 to 99 weight percent water or water and alcohol; and
from about 0.01 to 20 weight percent of a block copolymer of claim 1.

20. The hair styling composition of claim 19, wherein the hydrophobic block is a polyacrylate.

21. A method of preparing a hair styling composition, the method including preparing a film forming block copolymer having hydrophobic and hydrophilic blocks by copolymerizing in the presence of a free radical initiator:
(A) a polyfunctional chain extender having at least two functional groups, the reactivity of one functional group being substantially higher than that of the other functional group, wherein the polyfunctional chain extender has the formula:

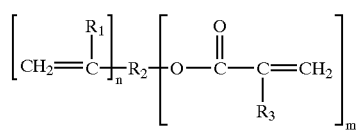

where n and m independently are integers from 1 to 4; $R_1$ and $R_3$ independently are H or alkyl; and $R_2$ is alkylene, cycloalkylene, arylene, —(CH$_2$—CH$_2$—O)$_p$ — where p=1 to 50, —CH$_2$(CH$_3$)—CH$_2$—O)$_p$— where p=1 to 50, amido, ester, or combinations thereof;

(B1) a first ethylenically unsaturated monomer or monomers which copolymerize in the presence of a free radical initiator preferentially with the functional group of the polyfunctional chain extender which has a higher reactivity to form a first block, wherein the first ethylenically unsaturated monomer comprises one or more of:
(1) acrylic acid or methacrylic acid; fumaric acid, itaconic acid or aconitic acid; maleic anhydride; and
(2) esters or amides respectively having the formula:

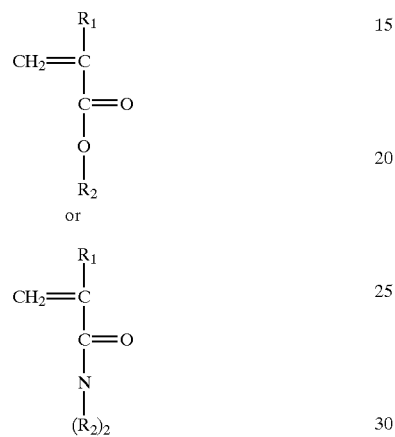

wherein R$_1$ is —H, —CH$_3$, or —CH$_2$CH$_3$; and R$_2$ is an aliphatic hydrocarbon functional group having at least one carbon, a polynuclear aromatic hydrocarbon group, an alkylaryl wherein the alkyl has one or more carbons, a haloalkyl having 4 or more carbons, a polyalkyleneoxy group wherein said alkylene is propylene or higher alkylene and there is at least 1 alkyleneoxy unit per hydrophobic moiety; α-olefins; vinyl alkylates; vinyl alkyl ethers; N-vinyl amides; or combinations thereof; and (B2) a second ethylenically unsaturated monomer or monomers which copolymerizes in the presence of a free radical initiator with the functional group of the polyfunctional chain extender which has the lesser reactivity to form a second block, wherein the second ethylenically unsaturated monomer comprises one or more of:
(1) an ethylenically unsaturated amide having the formula:

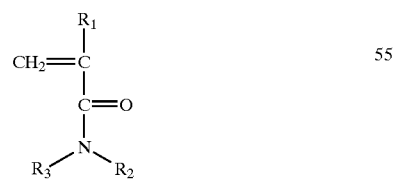

where R$_1$ is —H, —CH$_3$, —CH$_2$—CH$_3$, branched or linear alkyl, aryl, or cycloalkyl; and R$_2$ and R$_3$ independently are —H, —CH$_3$, —CH$_2$—CH$_3$, branched alkyl, linear alkyl, aryl, cycloalkyl, acid or salt functional, amino functional, or quaternized groups, or combinations thereof; and (2) ethylenically unsaturated carboxylic acids having at least one of the following formulas:

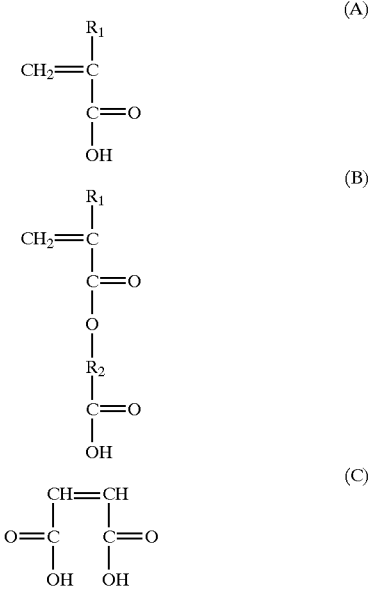

where R$_1$ is —H, —CH$_3$, or —CH$_2$CH$_3$; and R$_2$ is —[CH$_2$—]$_n$ where n is an integer from 1 to 40, linear or branched alkylene, cycloalkylene, arylene, polyethylene oxide; or polypropylene oxide; methacrylic acid, crotonic acid, itaconic acid and fumaric acid; half esters of maleic and fumaric acids; or combinations thereof; and wherein said (A) polyfunctional monomeric chain extender comprises from about 0.005 to 2 mole percent of the total monomers and substantially does not itself polymerize; said (B1) first ethylenically unsaturated monomer comprises from about 5 to about 95 mole percent of the total monomers; and said (B2) second ethylenically unsaturated monomer comprises from about 5 to about 70 mole percent of the total monomers; wherein said block copolymer has an average molecular weight up to 1,000,000, said first block is more hydrophobic than said second block, said first block has a molecular weight of at least 10,000 and a glass transition temperature of about 30° C. or less, and said second block has a molecular weight of at least 1,000 and glass transition temperature of greater than 30° C.

22. The method of claim 21, wherein the preparing of the copolymer includes:
adding to a reaction vessel, a solvent, a polyfunctional monomeric chain extender, the first ethylenically unsaturated monomer or monomers, and a free radical initiator;
reacting the monomers to form a first block; adding a second ethylenically unsaturated monomer or monomers having at least one carboxylic acid group; and,
reacting the monomers to form a second block and a copolymer having both hydrophobic and hydrophilic groups and at least two glass transition temperatures.

23. The method of claim 22, wherein the initiator is selected from the group consisting of azo-type initiators and peroxo-type initiators.

24. The method of claim 23, wherein the initiator is an azo-type initiator selected from the group consisting of azobis-dimethylvaleronitrile, azobis-isobutyronitrile, azobis-methylbutyronitrile, and combinations thereof.

25. The method of claim 23, wherein the initiator is a peroxo-type initiator selected from the group consisting of di-T butyl peroxide, T-butyl cumyl peroxide, T-butyl peroxypivalate, lauryl peroxide, cumene hydroperoxide, ethyl hexyl peroxodicarbonate, diisopropyl peroxydicarbonate, 4-(t-butylperoxylperoxycarbonyl)-3-hexyl-6-7-(t-butylperoxycarbonyl)heptyl cyclohexene, cumene hydroperoxide and t-butyl peroxyneodecanoate, t-butyl hydroperoxide, benzoyl peroxide, and combinations thereof.

26. The method of claim 25, wherein the initiator is t-butyl peroxypivalate.

27. The method of claim 23, wherein the initiator is at a concentration of from about 0.005 to 1 mole percent of the total monomers.

28. The method of claim 22, wherein the solvent is selected from the group consisting of water, hydrocarbons, alcohols, ethers, esters, aromatic solvents, glycols, glycol ethers, glycol esters, and combinations thereof.

29. The method of claim 28, wherein the solvent also includes water.

30. The method of claim 28, wherein the solvent is selected from the group consisting of water, ethyl alcohol, isopropyl alcohol, t-butyl alcohol, ethyl acetate, methyl acetate, butyl acetate, benzene, toluene, methylene choride, hexane, cyclohexane, mineral spirits, and combinations thereof.

31. The method of claim 28, wherein the solvent is isopropyl alcohol and water.

32. The method of claim 22, wherein the copolymer is produced in the same reaction vessel.

33. The method of claim 22, further including neutralizing the copolymer so that between 0.1 and 100 percent of the carboxylic acid groups are neutralized.

34. A method of preparing a hair styling composition, the method including:

preparing a film forming block copolymer of claim 1 and combining about 1–10 percent of said copolymer with from about 20 to 97 weight percent of water and from about 0 to 80 weight percent of an organic solvent.

35. The copolymer of claim 1, wherein the first ethylenically unsaturated monomer is selected from the group consisting of methyl acrylate, methyl methacrylate, butyl acrylate, ethyl acrylate, octyl acrylate, dodecyl acrylate, dodecyl methacrylate, tridecyl acrylate, tridecyl methacrylate, tetradecyl acrylate, tetradecyl methacrylate, octadecyl acrylate, octadecyl methacrylate, alkyl esters derived from the reactions of alkanols having from 2 to 20 carbon atoms with acrylic acid, methacrylic acid, maleic anhydride, fumaric acid, itaconic acid and aconitic acid, nonyl -phenyl acrylate, nonyl-α-phenyl methacrylate, dodecyl-α-phenyl acrylate and dodecyl-α-phenyl methacrylate, N-butyl acrylamide, T-butyl acrylamide, octyl acrylamide, N-octadecyl arylamide; N-octadecyl methacrylamide, N,N-dioctyl acrylamide, octene-1, decene-1, dodecene-1, hexadecene-1, vinyl laurate, vinyl stearate, dodecyl vinyl ether, hexadecyl vinyl ether, N-vinyl lauramide, N-vinyl stearamide, t-butyl styrene, and combinations thereof.

36. The copolymer of claim 1, wherein said first block has a glass transition temperature which is less than the glass transition temperature of said second block.

37. The copolymer of claim 1, wherein the polyfunctional monomer has a fast reacting unsaturated group of the acrylate or methacrylate type and a slower reacting group of the allyl type.

38. The copolymer of claim 1, wherein said polyfunctional monomer is allyl methacrylate.

39. The copolymer of claim 1, wherein the first ethylenically unsaturated monomers are a blend of hydrophobic and hydrophilic monomers.

40. The copolymer of claim 1, wherein the second ethylenically unsaturated monomers are a blend of hydrophilic, ionizable monomers.

41. The copolymer of claim 1, wherein the first ethylenically unsaturated monomers are a mixture of n-butyl acrylate and methacrylic acid.

42. The copolymer of claim 41, wherein said acid monomer comprises 50 mole % or less of said monomer mixture.

43. The copolymer of claim 1, wherein the second ethylenically unsaturated monomers are a blend of acrylic acid and methacrylic acid.

44. The copolymer of claim 1, wherein the first ethylenically unsaturated monomers are a mixture of n-butyl acrylate and methacrylic acid, the second ethylenically unsaturated monomers are a blend of acrylic acid and methacrylic acid, and the acid monomers comprise about 50 to about 70 mole % of the total monomers.

45. The copolymer of claim 39, wherein said hydrophilic monomer comprises 60% by weight or less of the blend of hydrophobic and hydrophilic monomers.

46. The copolymer of claim 1, wherein the first ethylenically unsaturated monomers are a mixture of n-butyl acrylate and methacrylic acid, the second ethylenically unsaturated monomers are a blend of acrylic acid and methacrylic acid, and the acid monomers comprise about 50 to about 50 mole % of the total monomers.

47. The copolymer of claim 1, wherein the second ethylenically unsaturated monomer is selected from the group consisting of vinylbenzyl sulfonic acid, vinylbenzyl trimethyl ammonium chloride, and 2-sulfoethyl methacrylate.

48. A method of improving wicking of a hair styling composition by incorporating therein 0.01% to 20% of the total weight of the composition of a block copolymer of claim 1.

49. A method of claim 48, wherein said block copolymer is incorporated in the amount of from 0.5% to 10%.

50. A method of increasing the volume of hair by applying thereto a hair formulation containing 0.01% to 20% of a block copolymer of claim 1.

51. A method of claim 50, wherein said block copolymer is used in the amount of from 0.5% to 10%.

52. A method of increasing the diameter of the hair by applying thereto a hair formulation containing 0.01% to 20% of a block copolymer of claim 1.

53. A method of claim 52, wherein said copolymer is used in the amount of from 0.5% to 10%.

54. A method of improving restylability of hair by applying thereto a hair styling composition containing 0.01% to 20% of the total weight of the composition of a block copolymer of claim 1.

55. A method of claim 54, wherein said copolymer is used in the amount of from 0.5% to 10%.

* * * * *